United States Patent
Stephanopoulos et al.

(10) Patent No.: US 9,181,539 B2
(45) Date of Patent: Nov. 10, 2015

(54) STRAINS FOR THE PRODUCTION OF FLAVONOIDS FROM GLUCOSE

(75) Inventors: Gregory Stephanopoulos, Winchester, MA (US); Christine Santos, Richmond, CA (US); Mattheos Koffas, Williamsville, NY (US)

(73) Assignees: Massachusetts Institute of Technology, Cambridge, MA (US); The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 13/101,462

(22) Filed: May 5, 2011

(65) Prior Publication Data

US 2012/0034661 A1 Feb. 9, 2012

Related U.S. Application Data

(60) Provisional application No. 61/332,593, filed on May 7, 2010.

(51) Int. Cl.

| | |
|---|---|
| C12P 17/06 | (2006.01) |
| C12N 1/20 | (2006.01) |
| C12N 1/00 | (2006.01) |
| C12N 15/00 | (2006.01) |
| C12N 5/02 | (2006.01) |
| C12N 5/07 | (2010.01) |
| C12N 5/04 | (2006.01) |
| C07H 21/04 | (2006.01) |
| C12N 9/88 | (2006.01) |
| C12N 9/10 | (2006.01) |
| C12N 9/90 | (2006.01) |
| C12N 9/00 | (2006.01) |

(52) U.S. Cl.
CPC ............... *C12N 9/88* (2013.01); *C12N 9/1029* (2013.01); *C12N 9/90* (2013.01); *C12N 9/93* (2013.01); *C12P 17/06* (2013.01)

(58) Field of Classification Search
CPC .......... C12N 9/1029; C12N 9/88; C12N 9/93; C12N 9/90; C12P 17/06
USPC ......... 435/125, 252.3, 252.33, 254.11, 254.2, 435/320.1, 325, 348, 419; 536/23.2
See application file for complete search history.

(56) References Cited

U.S. PATENT DOCUMENTS

2005/0208643 A1  9/2005  Schmidt-Dannert et al.
2011/0300588 A1  12/2011  Santos et al.

FOREIGN PATENT DOCUMENTS

WO   WO 2011/140344 A1   11/2011

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kimchi-Sarfaty et al., A "Silent" polymorphism in the MDR1 gene changes substrate specificty. Science, 2007, vol. 315: 525-528.*
Kisselev L., Polypeptide release factors in prokaryotes and eukaryotes: same function, different structure. Structure, 2002, vol. 10: 8-9.*
Nackley et al., Human Caechol-O-Methytransferase haplotypes modulate protein expression by altering mRNA secondary structure. Science, 2006, vol. 314: 1930-1933.*
Sauna et al., Silent polymorhisms speak: How they affect pharmacogenomics and the treatment of cancer. Cancer Res., 2007, vol. 67(20): 9609-9612.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
EMBL Submission; Accession No. D63577; Fujii; Aug. 15, 1995. 1 page.
Genbank Submission; Geneseq, EBI Accession No. ARK13239; Van Assema et al.; Nov. 27, 2008. 1 page.
Genbank Submission; Geneseq, EBI Accession No. AXK00331; Plesch et al.; Dec. 10, 2009. 2 pages.
Alper et al., Stephanopoulos G. Tuning genetic control through promoter engineering. Proc Natl Acad Sci U S A. Sep. 6, 2005;102(36):12678-83. Epub Aug. 25, 2005.
Forkmann et al., Metabolic engineering and applications of flavonoids. Curr Opin Biotechnol. Apr. 2001;12(2):155-60.
Fowler et al., Biosynthesis and biotechnological production of flavanones: current state and perspectives. Appl Microbiol Biotechnol. Jul. 2009;83(5):799-808. doi: 10.1007/s00253-009-2039-z. Epub May 28, 2009.
Fowler et al., Increased malonyl coenzyme A biosynthesis by tuning the *Escherichia coli* metabolic network and its application to flavanone production. Appl Environ Microbiol. Sep. 2009;75(18):5831-9.
Harborne et al., Advances in flavonoid research since 1992. Phytochemistry. Nov. 2000;55(6):481-504.
Hollman et al., Bioavailability and health effects of dietary flavonols in man. Arch Toxicol Suppl. 1998;20:237-48.
Jayaraj et al., GeMS: an advanced software package for designing synthetic genes. Nucleic Acids Res. May 23, 2005;33(9):3011-6.

(Continued)

*Primary Examiner* — Ganapathirama Raghu
(74) *Attorney, Agent, or Firm* — Wolf, Greenfield & Sacks, P.C.

(57) ABSTRACT

The invention relates to the production of flavonoids and flavonoid precursors in cells through recombinant expression of tyrosine ammonia lyase (TAL), 4-coumarate:CoA ligase (4CL), chalcone synthase (CHS), and chalcone isomerase (CHI).

19 Claims, 2 Drawing Sheets

(56) References Cited

OTHER PUBLICATIONS

Kane, Effects of rare codon clusters on high-level expression of heterologous proteins in *Escherichia coli*. Curr Opin Biotechnol. Oct. 1995;6(5):494-500.

Kaneko et al., Heterologous production of flavanones in *Escherichia coli*: potential for combinatorial biosynthesis of flavonoids in bacteria. J Ind Microbiol Biotechnol. Aug. 2003;30(8):456-61. Epub May 21, 2003.

Klein-Marcuschamer et al., Mutagenesis of the bacterial RNA polymerase alpha subunit for improvement of complex phenotypes. Appl Environ Microbiol. May 2009;75(9):2705-11. Epub Feb. 27, 2009.

Knekt et al., Flavonoid intake and coronary mortality in Finland: a cohort study. BMJ. Feb. 24, 1996;312(7029):478-81.

Kodumal et al., Total synthesis of long DNA sequences: synthesis of a contiguous 32-kb polyketide synthase gene cluster. Proc Natl Acad Sci U S A. Nov. 2, 2004;101(44):15573-8. Epub Oct. 20, 2004.

Leonard et al., Engineering central metabolic pathways for high-level flavonoid production in *Escherichia coli*. Appl Environ Microbiol. Jun. 2007;73(12):3877-86. Epub Apr. 27, 2007.

Leonard et al., Strain improvement of recombinant *Escherichia coli* for efficient production of plant flavonoids. Mol Pharm. Mar.-Apr. 2008;5(2):257-65. Epub Mar. 12, 2008.

Miyahisa et al., Efficient production of (2S)-flavanones by *Escherichia coli* containing an artificial biosynthetic gene cluster. Appl Microbiol Biotechnol. Sep. 2005;68(4):498-504. Epub Oct. 26, 2005. Epub Mar. 16, 2005.

Neidhardt et al., Culture medium for enterobacteria. J Bacteriol. Sep. 1974;119(3):736-47.

Pédelacq et al., Engineering and characterization of a superfolder green fluorescent protein. Nat Biotechnol. Jan. 2006;24(1):79-88. Epub Dec. 20, 2005. Erratum included.

Pfleger et al., Combinatorial engineering of intergenic regions in operons tunes expression of multiple genes. Nat Biotechnol. Aug. 2006;24(8):1027-32. Epub Jul. 16, 2006.

Santos et al., Optimization of a heterologous pathway for the production of flavonoids from glucose. Metab Eng. Jul. 2011;13(4):392-400. Doi: 10.1016/j.ymben.2011.02.002. Epub Feb. 12, 2011.

Sariaslani, Development of a combined biological and chemical process for production of industrial aromatics from renewable resources. Annu Rev Microbiol. 2007;61:51-69. First published online as Rev in Adv Apr. 24, 2007.

Schroeder et al., Contributions of conserved serine and tyrosine residues to catalysis, ligand binding, and cofactor processing in the active site of tyrosine ammonia lyase. Phytochemistry. May 2008;69(7):1496-506. Epub Mar. 17, 2008.

Takamura et al., Changes in the intracellular concentration of acetyl-CoA and malonyl-CoA in relation to the carbon and energy metabolism of *Escherichia coli* K12. J Gen Microbiol. Aug. 1988;134(8):2249-53.

Vannelli et al., Production of p-hydroxycinnamic acid from glucose in *Saccharomyces cerevisiae* and *Escherichia coli* by expression of heterologous genes from plants and fungi. Metab Eng. Mar. 2007;9(2):142-51. Epub Nov. 15, 2006.

Watts et al., Discovery of a substrate selectivity switch in tyrosine ammonia-lyase, a member of the aromatic amino acid lyase family. Chem Biol. Dec. 2006;13(12):1317-26.

Watts et al., Exploring recombinant flavonoid biosynthesis in metabolically engineered *Escherichia coli*. Chembiochem. Apr. 2, 2004;5(4):500-7.

Xue et al., Identification, characterization and functional expression of a tyrosine ammonia-lyase and its mutants from the photosynthetic bacterium *Rhodobacter sphaeroides*. J Ind Microbiol Biotechnol. Sep. 2007;34(9):599-604. Epub Jun. 30, 2007.

Xue et al., Improved production of p-hydroxycinnamic acid from tyrosine using a novel thermostable phenylalanine/tyrosine ammonia lyase enzyme. Enz Microb Tech. 2007; 42(1):58-64.

* cited by examiner

SEQUENCE LISTING

```
<160> NUMBER OF SEQ ID NOS: 35

<210> SEQ ID NO 1
<211> LENGTH: 29
<212> TYPE: DNA
<213> ORGANISM: artificial sequence
<220> FEATURE:
<223> OTHER INFORMATION: oligonucleotide primer

<400> SEQUENCE: 1
gctcggtacc atgctcgcca tgagccccc                                    29

<210> SEQ ID NO 2
<211> LENGTH: 34
<212> TYPE: DNA
<213> ORGANISM: artificial sequence
<220> FEATURE:
<223> OTHER INFORMATION: oligonucleotide primer

<400> SEQUENCE: 2
acgaagcttt tagacgggag attgctgcaa gagg                              34

<210> SEQ ID NO 3
<211> LENGTH: 28
<212> TYPE: DNA
<213> ORGANISM: artificial sequence
<220> FEATURE:
<223> OTHER INFORMATION: oligonucleotide primer
```

-continued

<400> SEQUENCE: 3
taaaccatgg tccgcagcga gtacgcag                              28

<210> SEQ ID NO 4
<211> LENGTH: 31
<212> TYPE: DNA
<213> ORGANISM: artificial sequence
<220> FEATURE:
<223> OTHER INFORMATION: oligonucleotide primer

<400> SEQUENCE: 4
acgaagcttt tatcgcggct ccctgagctg t                          31

<210> SEQ ID NO 5
<211> LENGTH: 31
<212> TYPE: DNA
<213> ORGANISM: artificial sequence
<220> FEATURE:
<223> OTHER INFORMATION: oligonucleotide primer

<400> SEQUENCE: 5
taaaccatgg tgatggctgg tgcttcttct t                          31

<210> SEQ ID NO 6
<211> LENGTH: 35
<212> TYPE: DNA
<213> ORGANISM: artificial sequence
<220> FEATURE:
<223> OTHER INFORMATION: oligonucleotide primer

<400> SEQUENCE: 6
gctcggtacc ttagagagga acgctgtgca agacg                      35

<210> SEQ ID NO 7
<211> LENGTH: 28
<212> TYPE: DNA
<213> ORGANISM: artificial sequence
<220> FEATURE:
<223> OTHER INFORMATION: oligonucleotide primer

<400> SEQUENCE: 7
gctcggtacc atggctgcgg ctgctgcc                              28

<210> SEQ ID NO 8
<211> LENGTH: 37
<212> TYPE: DNA
<213> ORGANISM: artificial sequence
<220> FEATURE:
<223> OTHER INFORMATION: oligonucleotide primer

<400> SEQUENCE: 8
acgaagcttt tacacaataa taccgtggct caacacg                    37

<210> SEQ ID NO 9
<211> LENGTH: 50
<212> TYPE: DNA
<213> ORGANISM: artificial sequence
<220> FEATURE:
<223> OTHER INFORMATION: oligonucleotide primer

<400> SEQUENCE: 9
acgaagctta atcctaggaa ctgaaatgag ctgttgacaa ttaatcatcc       50

<210> SEQ ID NO 10
<211> LENGTH: 51

<212> TYPE: DNA
<213> ORGANISM: artificial sequence
<220> FEATURE:
<223> OTHER INFORMATION: oligonucleotide primer

<400> SEQUENCE: 10
acgaagcttc ttggatcccg atccggaaat tatcgcggct ccctgagctg t    51

<210> SEQ ID NO 11
<211> LENGTH: 50
<212> TYPE: DNA
<213> ORGANISM: artificial sequence
<220> FEATURE:
<223> OTHER INFORMATION: oligonucleotide primer

<400> SEQUENCE: 11
gagttcgaac gatgtacaaa ctgaaatgag ctgttgacaa ttaatcatcc    50

<210> SEQ ID NO 12
<211> LENGTH: 61
<212> TYPE: DNA
<213> ORGANISM: artificial sequence
<220> FEATURE:
<223> OTHER INFORMATION: oligonucleotide primer

<400> SEQUENCE: 12
gctagcttcg tacgtgctga gcatatcaat tgattacaca ataataccgt ggctcaacac    60
g    61

<210> SEQ ID NO 13
<211> LENGTH: 75
<212> TYPE: DNA
<213> ORGANISM: artificial sequence
<220> FEATURE:
<223> OTHER INFORMATION: oligonucleotide primer

<400> SEQUENCE: 13
gagttcgaac tcgagatact agtgtagatc tttggcctcg ctggccatgc tagcttcgta    60
cgtgctgagc atatc    75

<210> SEQ ID NO 14
<211> LENGTH: 32
<212> TYPE: DNA
<213> ORGANISM: artificial sequence
<220> FEATURE:
<223> OTHER INFORMATION: oligonucleotide primer

<400> SEQUENCE: 14
cttggatccg ccgacatcat aacggttctg gc    32

<210> SEQ ID NO 15
<211> LENGTH: 45
<212> TYPE: DNA
<213> ORGANISM: artificial sequence
<220> FEATURE:
<223> OTHER INFORMATION: oligonucleotide primer

<400> SEQUENCE: 15
cttggatccg agttcgaact cgagatacta gtgtagatct ttggc    45

<210> SEQ ID NO 16
<211> LENGTH: 19
<212> TYPE: DNA
<213> ORGANISM: artificial sequence
<220> FEATURE:

<223> OTHER INFORMATION: oligonucleotide primer

<400> SEQUENCE: 16
taaaccatgg cgcctcgcc                                                19

<210> SEQ ID NO 17
<211> LENGTH: 36
<212> TYPE: DNA
<213> ORGANISM: artificial sequence
<220> FEATURE:
<223> OTHER INFORMATION: oligonucleotide primer

<400> SEQUENCE: 17
aatgtcgact tatgccagca tcttcagcag aacatt                              36

<210> SEQ ID NO 18
<211> LENGTH: 30
<212> TYPE: DNA
<213> ORGANISM: artificial sequence
<220> FEATURE:
<223> OTHER INFORMATION: oligonucleotide primer

<400> SEQUENCE: 18
gcactaacat atgggtgact gcgttgcccc                                     30

<210> SEQ ID NO 19
<211> LENGTH: 27
<212> TYPE: DNA
<213> ORGANISM: artificial sequence
<220> FEATURE:
<223> OTHER INFORMATION: oligonucleotide primer

<400> SEQUENCE: 19
aatcctaggt tacttcggca ggtcgcc                                        27

<210> SEQ ID NO 20
<211> LENGTH: 23
<212> TYPE: DNA
<213> ORGANISM: artificial sequence
<220> FEATURE:
<223> OTHER INFORMATION: oligonucleotide primer

<400> SEQUENCE: 20
taacatatgg tgatggctgg tgc                                            23

<210> SEQ ID NO 21
<211> LENGTH: 34
<212> TYPE: DNA
<213> ORGANISM: artificial sequence
<220> FEATURE:
<223> OTHER INFORMATION: oligonucleotide primer

<400> SEQUENCE: 21
aatcctaggt tagagaggaa cgctgtgcaa gacg                                34

<210> SEQ ID NO 22
<211> LENGTH: 22
<212> TYPE: DNA
<213> ORGANISM: artificial sequence
<220> FEATURE:
<223> OTHER INFORMATION: oligonucleotide primer

<400> SEQUENCE: 22
tataccatgg ctgcggctgc tg                                             22

```
<210> SEQ ID NO 23
<211> LENGTH: 39
<212> TYPE: DNA
<213> ORGANISM: artificial sequence
<220> FEATURE:
<223> OTHER INFORMATION: oligonucleotide primer

<400> SEQUENCE: 23
taagcggccg cttacacaat aataccgtgg ctcaacacg                    39

<210> SEQ ID NO 24
<211> LENGTH: 33
<212> TYPE: DNA
<213> ORGANISM: artificial sequence
<220> FEATURE:
<223> OTHER INFORMATION: oligonucleotide primer

<400> SEQUENCE: 24
catgacgtcc cgcttacaga caagctgtga ccg                          33

<210> SEQ ID NO 25
<211> LENGTH: 27
<212> TYPE: DNA
<213> ORGANISM: artificial sequence
<220> FEATURE:
<223> OTHER INFORMATION: oligonucleotide primer

<400> SEQUENCE: 25
gcttcgtacg tgctgagcat atcaatt                                 27

<210> SEQ ID NO 26
<211> LENGTH: 35
<212> TYPE: DNA
<213> ORGANISM: artificial sequence
<220> FEATURE:
<223> OTHER INFORMATION: oligonucleotide primer

<400> SEQUENCE: 26
taacggccgg ccccgacatc ataacggttc tggca                        35

<210> SEQ ID NO 27
<211> LENGTH: 36
<212> TYPE: DNA
<213> ORGANISM: artificial sequence
<220> FEATURE:
<223> OTHER INFORMATION: oligonucleotide primer

<400> SEQUENCE: 27
taaggatccc aacagataaa acgaaaggcc cagtct                       36

<210> SEQ ID NO 28
<211> LENGTH: 14
<212> TYPE: DNA
<213> ORGANISM: artificial sequence
<220> FEATURE:
<223> OTHER INFORMATION: oligonucleotide primer

<400> SEQUENCE: 28
gtacgcgcat gcgc                                               14

<210> SEQ ID NO 29
<211> LENGTH: 14
<212> TYPE: DNA
<213> ORGANISM: artificial sequence
<220> FEATURE:
<223> OTHER INFORMATION: oligonucleotide primer
```

```
<400> SEQUENCE: 29
gatcgcgcat gcgc                                                           14

<210> SEQ ID NO 30
<211> LENGTH: 675
<212> TYPE: DNA
<213> ORGANISM: artificial sequence
<220> FEATURE:
<223> OTHER INFORMATION: P. lobata chalcone isomerase

<400> SEQUENCE: 30
atggctgcgg ctgctgccgt ggcgaccatt agcgcggtgc aagtggagtt tctggaattt         60
ccagcggtag tgaccagccc ggcatcaggc cgtacctatt ttcttggtgg cgctggggag        120
cgtggcctga cgattgaggg caagtttatc aagttcaccg gcattggcgt gtatttggaa        180
gataaggcgg ttagctccct ggcggcgaaa tggaaaggca aaccgagcga agaactggtg        240 gagacccctgg acttctaccg ggatatcata agcggtccct tcgagaaact gatccgtggc        300
agcaaaattc tgccactgtc gggcgtcgaa tacagcaaga aagtgatgga aaactgcgtg        360
gcgcatatga aaagcgtcgg aacctatggc gatgcggaag ccgctgccat cgagaagttc        420
gcggaggcct tcaaaaacgt gaattttcaa cctggcgcga ccgtgtttta tcggcaaagc        480
ccagatggcg ttctgggcct gagtttcagc gaggatgtga ccattcccga taatgaagcg        540
gcggtgattg aaaacaaagc cgtctccgct gcggtgttag aaaccatgat ggcgaacat         600 gcagtaagcc ccgatctgaa acgtagcttg gcgagccggt tacccgccgt gttgagccac        660
ggtattattg tgtaa                                                        675

<210> SEQ ID NO 31
<211> LENGTH: 224
<212> TYPE: PRT
<213> ORGANISM: artificial sequence
<220> FEATURE:
<223> OTHER INFORMATION: P. lobata chalcone isomerase

<400> SEQUENCE: 31

Met Ala Ala Ala Ala Val Ala Thr Ile Ser Ala Val Gln Val Glu
1               5                   10                  15

Phe Leu Glu Phe Pro Ala Val Val Thr Ser Pro Ala Ser Gly Arg Thr
            20                  25                  30

Tyr Phe Leu Gly Gly Ala Gly Glu Arg Gly Leu Thr Ile Glu Gly Lys
        35                  40                  45

Phe Ile Lys Phe Thr Gly Ile Gly Val Tyr Leu Glu Asp Lys Ala Val
    50                  55                  60

Ser Ser Leu Ala Ala Lys Trp Lys Gly Lys Pro Ser Glu Glu Leu Val
65                  70                  75                  80

Glu Thr Leu Asp Phe Tyr Arg Asp Ile Ile Ser Gly Pro Phe Glu Lys
                85                  90                  95

Leu Ile Arg Gly Ser Lys Ile Leu Pro Leu Ser Gly Val Glu Tyr Ser
            100                 105                 110

Lys Lys Val Met Glu Asn Cys Val Ala His Met Lys Ser Val Gly Thr
        115                 120                 125

Tyr Gly Asp Ala Glu Ala Ala Ala Ile Glu Lys Phe Ala Glu Ala Phe
    130                 135                 140

Lys Asn Val Asn Phe Gln Pro Gly Ala Thr Val Phe Tyr Arg Gln Ser
145                 150                 155                 160

Pro Asp Gly Val Leu Gly Leu Ser Phe Ser Glu Asp Val Thr Ile Pro
```

165                 170                 175
Asp Asn Glu Ala Ala Val Ile Glu Asn Lys Ala Val Ser Ala Ala Val
            180                 185                 190

Leu Glu Thr Met Ile Gly Glu His Ala Val Ser Pro Asp Leu Lys Arg
        195                 200                 205

Ser Leu Ala Ser Arg Leu Pro Ala Val Leu Ser His Gly Ile Ile Val
    210                 215                 220

<210> SEQ ID NO 32
<211> LENGTH: 2082
<212> TYPE: DNA
<213> ORGANISM: artificial sequence
<220> FEATURE:
<223> OTHER INFORMATION: R. glutinis tyrosine ammonia lyase

<400> SEQUENCE: 32

| | | | | | |
|---|---|---|---|---|---|
| atggcgcctc | gcccgacttc | gcaaagccag | gcccgcactt | gcccgacgac | gcaggttacc | 60 |
| caagttgata | tcgttgagaa | aatgttggcg | gctcctactg | atagcacgct | ggagctggac | 120 |
| ggttatagcc | tgaatctggg | tgatgtcgtg | agcgctgcgc | gtaagggtcg | tcctgtccgt | 180 |
| gtcaaagata | gcgatgaaat | ccgcagcaaa | atcgacaaga | gcgttgaatt | cctgcgcagc | 240 |
| caactgagca | tgtcggttta | cggtgtgacg | accggctttg | gcggctccgc | ggacacgcgc | 300 |
| acggaggacg | caattagcct | gcaaaaggcg | ttgctggaac | accagctgtg | tggtgtgttg | 360 |
| ccgagcagct | tcgacagctt | tcgcttgggt | cgtggtctgg | agaatagcct | gccgttggaa | 420 |
| gtcgttcgcg | gtgcaatgac | cattcgtgtg | aattcgctga | ccgtggcca | tagcgctgtt | 480 |
| cgtctggttg | ttctggaagc | actgacgaac | tttctgaacc | acggtattac | cccgattgtt | 540 |
| ccgctgcgcg | gtacgatctc | cgcgagcggc | gatctgtctc | cactgtcgta | cattgcagcg | 600 |
| gcgattagcg | gtcacccgga | tagcaaagtt | cacgtggtcc | atgaaggcaa | agagaagatc | 660 |
| ctgtacgcgc | gcgaagcgat | ggcgctgttt | aacctggagc | cggtggtttt | gggtccgaag | 720 |
| gagggcctgg | gtctggtgaa | tggtacggca | gtctccgcga | gcatggcaac | gctggcactg | 780 |
| cacgacgcgc | atatgttgag | cctgttgagc | caatcgctga | ccgcgatgac | cgtgaggcg | 840 |
| atggtcggtc | acgcgggcag | cttccatcca | ttcctgcacg | atgttacgcg | tccgcacccg | 900 |
| acgcaaatcg | aggtcgcggg | taacattcgc | aaactgctgg | agggctcgcg | cttcgcggtc | 960 |
| caccacgagg | aagaggttaa | ggtcaaggat | gatgaaggca | ttttgcgtca | ggatcgttat | 1020 |
| ccgttgcgca | cgagcccgca | atggttgggt | ccgctggtgt | ccgacctgat | tcacgctcat | 1080 |
| gccgtcttga | cgatcgaagc | gggtcaaagc | accaccgata | ccccactgat | cgatgttgag | 1140 |
| aataagacca | gccatcacgg | tggcaacttt | caagcggcag | cggttgccaa | cacgatggaa | 1200 |
| aagacccgtc | tgggcttggc | ccaaatcggt | aaactgaatt | tcacccagct | gacggagatg | 1260 |
| ctgaacgcgg | gcatgaatcg | tggcttgccg | agctgcctgg | cggctgaaga | cccatccctg | 1320 |
| agctatcatt | gcaaaggtct | ggacattgcg | cggctgcat | atacgagcga | actgggccac | 1380 |
| ctggctaacc | cggtcaccac | ccacgtccaa | ccggctgaaa | tggcaaacca | ggcggtgaat | 1440 |
| agcttggcgt | tgattagcgc | acgtcgtacc | acggaatcta | acgacgttct | gtccctgctg | 1500 |
| ctggcaacgc | acctgtactg | cgtgctgcag | gcgatcgacc | tgcgtgcgat | tgagttcgag | 1560 |
| ttcaagaaac | agtttggtcc | tgccattgtt | agcctgatcg | accaacactt | tggtagcgcg | 1620 |
| atgacgggta | gcaatctgcg | tgatgagctg | gttgaaaagg | tcaataagac | tctgccaaag | 1680 |
| cgtttggagc | aaaccaatag | ctacgatctg | gttccgcgct | ggcacgacgc | ttttagcttc | 1740 |

-continued

```
gctgcaggca ctgttgtcga ggttctgtcc agcacgagcc tgagcttggc ggccgtgaac   1800
gcatggaagg ttgcggcagc cgagagcgcg atctccttga cgcgccaggt ccgtgaaacg   1860
ttttggtccg ctgcaagcac ctccagcccg gcgttgtctt acttgagccc gcgcacgcag   1920
atcctgtacg catttgtgcg tgaggaactg ggtgtcaaag cccgccgtgg tgacgtcttc   1980
ttgggtaaac aagaagttac catcggcagc aacgttagca agatttacga agccatcaag   2040
agcggccgta tcaacaatgt tctgctgaag atgctggcat aa                     2082
```

```
<210> SEQ ID NO 33
<211> LENGTH: 693
<212> TYPE: PRT
<213> ORGANISM: artificial sequence
<220> FEATURE:
<223> OTHER INFORMATION: R. glutinis tyrosine ammonia lyase

<400> SEQUENCE: 33
```

Met Ala Pro Arg Pro Thr Ser Gln Ser Gln Ala Arg Thr Cys Pro Thr
1               5                   10                  15

Thr Gln Val Thr Gln Val Asp Ile Val Glu Lys Met Leu Ala Ala Pro
                20                  25                  30

Thr Asp Ser Thr Leu Glu Leu Asp Gly Tyr Ser Leu Asn Leu Gly Asp
            35                  40                  45

Val Val Ser Ala Ala Arg Lys Gly Arg Pro Val Arg Val Lys Asp Ser
        50                  55                  60

Asp Glu Ile Arg Ser Lys Ile Asp Lys Ser Val Glu Phe Leu Arg Ser
65                  70                  75                  80

Gln Leu Ser Met Ser Val Tyr Gly Val Thr Thr Gly Phe Gly Gly Ser
                85                  90                  95

Ala Asp Thr Arg Thr Glu Asp Ala Ile Ser Leu Gln Lys Ala Leu Leu
            100                 105                 110

Glu His Gln Leu Cys Gly Val Leu Pro Ser Ser Phe Asp Ser Phe Arg
        115                 120                 125

Leu Gly Arg Gly Leu Glu Asn Ser Leu Pro Leu Glu Val Val Arg Gly
    130                 135                 140

Ala Met Thr Ile Arg Val Asn Ser Leu Thr Arg Gly His Ser Ala Val
145                 150                 155                 160

Arg Leu Val Val Leu Glu Ala Leu Thr Asn Phe Leu Asn His Gly Ile
                165                 170                 175

Thr Pro Ile Val Pro Leu Arg Gly Thr Ile Ser Ala Ser Gly Asp Leu
            180                 185                 190

Ser Pro Leu Ser Tyr Ile Ala Ala Ala Ile Ser Gly His Pro Asp Ser
        195                 200                 205

Lys Val His Val His Glu Gly Lys Glu Lys Ile Leu Tyr Ala Arg
    210                 215                 220

Glu Ala Met Ala Leu Phe Asn Leu Glu Pro Val Val Leu Gly Pro Lys
225                 230                 235                 240

Glu Gly Leu Gly Leu Val Asn Gly Thr Ala Val Ser Ala Ser Met Ala
                245                 250                 255

Thr Leu Ala Leu His Asp Ala His Met Leu Ser Leu Leu Ser Gln Ser
            260                 265                 270

Leu Thr Ala Met Thr Val Glu Ala Met Val Gly His Ala Gly Ser Phe
        275                 280                 285

His Pro Phe Leu His Asp Val Thr Arg Pro His Pro Thr Gln Ile Glu
    290                 295                 300

```
Val Ala Gly Asn Ile Arg Lys Leu Leu Glu Gly Ser Arg Phe Ala Val
305                 310                 315                 320

His His Glu Glu Glu Val Lys Val Lys Asp Asp Glu Gly Ile Leu Arg
            325                 330                 335

Gln Asp Arg Tyr Pro Leu Arg Thr Ser Pro Gln Trp Leu Gly Pro Leu
            340                 345                 350

Val Ser Asp Leu Ile His Ala His Ala Val Leu Thr Ile Glu Ala Gly
            355                 360                 365

Gln Ser Thr Thr Asp Asn Pro Leu Ile Asp Val Glu Asn Lys Thr Ser
            370                 375                 380

His His Gly Gly Asn Phe Gln Ala Ala Val Ala Asn Thr Met Glu
385                 390                 395                 400

Lys Thr Arg Leu Gly Leu Ala Gln Ile Gly Lys Leu Asn Phe Thr Gln
                405                 410                 415

Leu Thr Glu Met Leu Asn Ala Gly Met Asn Arg Gly Leu Pro Ser Cys
                420                 425                 430

Leu Ala Ala Glu Asp Pro Ser Leu Ser Tyr His Cys Lys Gly Leu Asp
            435                 440                 445

Ile Ala Ala Ala Ala Tyr Thr Ser Glu Leu Gly His Leu Ala Asn Pro
450                 455                 460

Val Thr Thr His Val Gln Pro Ala Glu Met Ala Asn Gln Ala Val Asn
465                 470                 475                 480

Ser Leu Ala Leu Ile Ser Ala Arg Arg Thr Thr Glu Ser Asn Asp Val
                485                 490                 495

Leu Ser Leu Leu Leu Ala Thr His Leu Tyr Cys Val Leu Gln Ala Ile
            500                 505                 510

Asp Leu Arg Ala Ile Glu Phe Glu Phe Lys Lys Gln Phe Gly Pro Ala
            515                 520                 525

Ile Val Ser Leu Ile Asp Gln His Phe Gly Ser Ala Met Thr Gly Ser
530                 535                 540

Asn Leu Arg Asp Glu Leu Val Glu Lys Val Asn Lys Thr Leu Ala Lys
545                 550                 555                 560

Arg Leu Glu Gln Thr Asn Ser Tyr Asp Leu Val Pro Arg Trp His Asp
                565                 570                 575

Ala Phe Ser Phe Ala Ala Gly Thr Val Val Glu Val Leu Ser Ser Thr
            580                 585                 590

Ser Leu Ser Leu Ala Ala Val Asn Ala Trp Lys Val Ala Ala Ala Glu
            595                 600                 605

Ser Ala Ile Ser Leu Thr Arg Gln Val Arg Glu Thr Phe Trp Ser Ala
610                 615                 620

Ala Ser Thr Ser Ser Pro Ala Leu Ser Tyr Leu Ser Pro Arg Thr Gln
625                 630                 635                 640

Ile Leu Tyr Ala Phe Val Arg Glu Glu Leu Gly Val Lys Ala Arg Arg
                645                 650                 655

Gly Asp Val Phe Leu Gly Lys Gln Glu Val Thr Ile Gly Ser Asn Val
            660                 665                 670

Ser Lys Ile Tyr Glu Ala Ile Lys Ser Gly Arg Ile Asn Asn Val Leu
            675                 680                 685

Leu Lys Met Leu Ala
            690

<210> SEQ ID NO 34
<211> LENGTH: 1635
<212> TYPE: DNA
```

```
<213> ORGANISM: artificial sequence
<220> FEATURE:
<223> OTHER INFORMATION: P. crispus 4-coumarate:coA ligase

<400> SEQUENCE: 34
atgggtgact gcgttgcccc gaaagaggat ctgatcttcc gcagcaaact gccggacatt      60
tacattccaa agcatctgcc gctgcatacg tattgttttg agaatatcag caaggttggc     120
gacaagagct gtctgatcaa cggcgcaacc ggcgaaacgt ttacctacag ccaggtcgag     180
ctgctgtccc gtaaagttgc cagcggcctg aacaagctgg gcattcaaca aggtgatacc     240
attatgctgt tgctgccgaa ttccccggag tactttttcg ctttcctggg tgcgagctat     300
cgcggtgcaa tcagcaccat ggcgaatcca ttctttacca gcgcagaagt gatcaagcaa     360
ctgaaagcga gccaagcgaa gctgattatc acccaggcat gctatgttga caaggtcaag     420
gactacgcag cggagaaaaa catccagatc atttgtattg acgatgcacc gcaggattgc     480
ctgcacttta gcaagctgat ggaagcggat gagagcgaaa tgccggaagt ggtcattaac     540
agcgatgatg tggtggcatt gccgtacagc tctggcacca ccggcctgcc gaaaggcgtt     600
atgctgaccc acaagggtct ggttacgagc gttgcacaac aggtggatgg tgataacccg     660
aacctgtata tgcactccga ggatgtcatg atctgcatcc tgccactgtt ccatatctat     720
agcctgaacg ctgttctgtg ttgtggtctg cgtgcgggcg tcaccattct gatcatgcaa     780
aagttcgaca ttgtgccgtt tctggagctg attcagaagt ataaggttac gattggtccg     840
tttgtcccgc cgatcgtgct ggccatcgcg aaaagcccgg tcgttgacaa gtacgacttg     900
tctagcgtgc gcaccgtcat gagcggtgca gcgccgctgg gtaaagagtt ggaggacgct     960
gtccgtgcga aattcccgaa cgcgaagctg ggtcaaggct atggcatgac cgaagccggt    1020
ccggtcctgg cgatgtgtct ggcgttcgcc aaagagccgt atgagattaa gtctggcgca    1080
tgcggtaccg ttgtgcgtaa tgccgagatg aaaatcgttg acccagaaac gaatgcgtct    1140
ctgccgcgta atcagcgtgg tgagatttgc atccgtggtg atcagattat gaaaggttac    1200
ctgaatgacc cggaaagcac ccgcaccacg atcgacgaag agggttggtt gcacacgggt    1260
gacattggtt tcatcgacga tgacgatgaa ctgttcattg tcgatcgttt gaaagaaatc    1320
attaagtaca aggttttca gttgctccg gcggagttgg aagcactgct gctgacgcac    1380
ccgacgatca gcgatgccgc ggtggttccg atgattgacg agaaagcggg tgaagtgcca    1440
gtggcgtttg tcgtgcgtac caatggtttt accacgaccg aagaagaaat caaacaattt    1500
gtgagcaaac aggtcgtgtt ctacaaacgt atcttccgcg tcttcttcgt tgacgctatt    1560
ccgaaatccc cgagcggcaa gattttgcgt aaggatctgc gcgctcgtat tgcgagcggc    1620
gacctgccga agtaa                                                     1635

<210> SEQ ID NO 35
<211> LENGTH: 544
<212> TYPE: PRT
<213> ORGANISM: artificial sequence
<220> FEATURE:
<223> OTHER INFORMATION: P. crispus 4-coumarate:coA ligase

<400> SEQUENCE: 35

Met Gly Asp Cys Val Ala Pro Lys Glu Asp Leu Ile Phe Arg Ser Lys
1               5                   10                  15

Leu Pro Asp Ile Tyr Ile Pro Lys His Leu Pro Leu His Thr Tyr Cys
            20                  25                  30

Phe Glu Asn Ile Ser Lys Val Gly Asp Lys Ser Cys Leu Ile Asn Gly
```

```
                    35                  40                  45
Ala Thr Gly Glu Thr Phe Thr Tyr Ser Gln Val Glu Leu Leu Ser Arg
 50                      55                      60

Lys Val Ala Ser Gly Leu Asn Lys Leu Gly Ile Gln Gln Gly Asp Thr
 65                  70                  75                  80

Ile Met Leu Leu Leu Pro Asn Ser Pro Glu Tyr Phe Phe Ala Phe Leu
                     85                  90                  95

Gly Ala Ser Tyr Arg Gly Ala Ile Ser Thr Met Ala Asn Pro Phe Phe
                100                 105                 110

Thr Ser Ala Glu Val Ile Lys Gln Leu Lys Ala Ser Gln Ala Lys Leu
                115                 120                 125

Ile Ile Thr Gln Ala Cys Tyr Val Asp Lys Val Lys Asp Tyr Ala Ala
                130                 135                 140

Glu Lys Asn Ile Gln Ile Ile Cys Ile Asp Asp Ala Pro Gln Asp Cys
145                 150                 155                 160

Leu His Phe Ser Lys Leu Met Glu Ala Asp Glu Ser Glu Met Pro Glu
                165                 170                 175

Val Val Ile Asn Ser Asp Asp Val Val Ala Leu Pro Tyr Ser Ser Gly
                180                 185                 190

Thr Thr Gly Leu Pro Lys Gly Val Met Leu Thr His Lys Gly Leu Val
                195                 200                 205

Thr Ser Val Ala Gln Gln Val Asp Gly Asp Asn Pro Asn Leu Tyr Met
210                 215                 220

His Ser Glu Asp Val Met Ile Cys Ile Leu Pro Leu Phe His Ile Tyr
225                 230                 235                 240

Ser Leu Asn Ala Val Leu Cys Cys Gly Leu Arg Ala Gly Val Thr Ile
                245                 250                 255

Leu Ile Met Gln Lys Phe Asp Ile Val Pro Phe Leu Glu Leu Ile Gln
                260                 265                 270

Lys Tyr Lys Val Thr Ile Gly Pro Phe Val Pro Pro Ile Val Leu Ala
                275                 280                 285

Ile Ala Lys Ser Pro Val Val Asp Lys Tyr Asp Leu Ser Ser Val Arg
                290                 295                 300

Thr Val Met Ser Gly Ala Ala Pro Leu Gly Lys Glu Leu Glu Asp Ala
305                 310                 315                 320

Val Arg Ala Lys Phe Pro Asn Ala Lys Leu Gly Gln Gly Tyr Gly Met
                325                 330                 335

Thr Glu Ala Gly Pro Val Leu Ala Met Cys Leu Ala Phe Ala Lys Glu
                340                 345                 350

Pro Tyr Glu Ile Lys Ser Gly Ala Cys Gly Thr Val Val Arg Asn Ala
                355                 360                 365

Glu Met Lys Ile Val Asp Pro Glu Thr Asn Ala Ser Leu Pro Arg Asn
                370                 375                 380

Gln Arg Gly Glu Ile Cys Ile Arg Gly Asp Gln Ile Met Lys Gly Tyr
385                 390                 395                 400

Leu Asn Asp Pro Glu Ser Thr Arg Thr Thr Ile Asp Glu Glu Gly Trp
                    405                 410                 415

Leu His Thr Gly Asp Ile Gly Phe Ile Asp Asp Asp Glu Leu Phe
                420                 425                 430

Ile Val Asp Arg Leu Lys Glu Ile Ile Lys Tyr Lys Gly Phe Gln Val
                435                 440                 445

Ala Pro Ala Glu Leu Glu Ala Leu Leu Leu Thr His Pro Thr Ile Ser
450                 455                 460
```

```
Asp Ala Ala Val Val Pro Met Ile Asp Glu Lys Ala Gly Glu Val Pro
465                 470                 475                 480

Val Ala Phe Val Val Arg Thr Asn Gly Phe Thr Thr Thr Glu Glu Glu
            485                 490                 495

Ile Lys Gln Phe Val Ser Lys Gln Val Val Phe Tyr Lys Arg Ile Phe
        500                 505                 510

Arg Val Phe Phe Val Asp Ala Ile Pro Lys Ser Pro Ser Gly Lys Ile
        515                 520                 525

Leu Arg Lys Asp Leu Arg Ala Arg Ile Ala Ser Gly Asp Leu Pro Lys
    530                 535                 540
```

STRAINS FOR THE PRODUCTION OF FLAVONOIDS FROM GLUCOSE

RELATED APPLICATION

This application claims the benefit under 35 U.S.C. §119 (e) of U.S. Provisional Application Ser. No. 61/332,593, filed on May 7, 2010, the entire contents of which is incorporated by reference herein in its entirety.

GOVERNMENT INTEREST

This invention was made with government support under Grant Nos. DGE0202745, DGE0645960, and CBET0756601 awarded by the National Science Foundation, and under Grant No. DE-FC36-07GO17058 awarded by the Department of Energy. The government has certain rights in this invention.

FIELD OF THE INVENTION

The invention relates to the production of flavonoids and flavonoid precursors through recombinant gene expression.

BACKGROUND OF THE INVENTION

The development of efficient microbial processes for the production of flavonoids has been a common metabolic engineering goal for the past several years, primarily due to the purported health-promoting effects of these compounds. Although significant strides have been made recently in improving strain titers and yields, current fermentation strategies unfortunately suffer from two major drawbacks—1) the requirement for expensive phenylpropanoic precursors supplemented into the media and 2) the need for two separate media formulations for biomass/protein generation and flavonoid production.

SUMMARY OF THE INVENTION

In this study, we detail the construction of a series of strains capable of bypassing both of these problems. A four-step heterologous pathway consisting of the enzymes tyrosine ammonia lyase (TAL), 4-coumarate:CoA ligase (4CL), chalcone synthase (CHS), and chalcone isomerase (CHI) was assembled within two engineered L-tyrosine overproducers in order to enable the production of the main flavonoid precursor naringenin directly from glucose. During the course of this investigation, we discovered that unexpectedly extensive optimization of both enzyme sources and relative gene expression levels was required to achieve high quantities of both p-coumaric acid and naringenin accumulation. Once this metabolic balance was achieved, however, such strains were found to be capable of producing 29 mg/l naringenin from glucose and up to 84 mg/l naringenin with the addition of the fatty acid enzyme inhibitor, cerulenin. These results were obtained through cultivation in a single minimal medium formulation without additional precursor supplementation, thus paving the way for the development of a simple and economical process for the microbial production of flavonoids.

According to certain aspects of the invention, cells are provided that recombinantly express genes encoding tyrosine ammonia lyase (TAL), 4-coumarate:CoA ligase (4CL), chalcone synthase (CHS), and chalcone isomerase (CHI). In some embodiments, the gene encoding TAL is a yeast gene or a bacterial gene, optionally a *Rhodotorula glutinis* gene or a *Rhodobacter sphaeroides* gene. In some embodiments, the gene encoding 4CL is a plant gene or a bacterial gene, optionally a *Petroselinum crispus* gene or a *Streptomyces coelicolor* gene. In some embodiments, the gene encoding CHS and/or the gene encoding CHI is a plant gene, optionally a *Petunia hybrida* gene or an *Arabidopsis thaliana* gene. In some embodiments, the gene encoding CHI is a *Medicago sativa* gene or a *Pueraria lobata* gene.

In some embodiments, the genes encoding TAL, 4CL, CHS, and/or CHI are expressed from a single polycistronic operon, or wherein each of the genes is expressed from a separate promoter. Optionally, one or more of the separate promoters is a trc promoter, a T7 promoter, or a constitutive promoter, optionally $P_{GAP}$.

In some embodiments, the cell is a prokaryotic cell, and optionally the cell is a strain previously engineered for high endogenous L-tyrosine production or p-coumaric acid synthesis. Preferably the endogenous L-tyrosine production is at least about 250 milligrams/liter. Examples of strains that produce high levels of L-tyrosine or that are engineered for high endogenous L-tyrosine production include the P2 and rpoA14$^R$ strains described herein.

In some embodiments, the cell is a bacterial cell, optionally an *E. coli* cell. In some embodiments, one or more of the genes encoding TAL, 4CL, CHS, and/or CHI is a synthetic gene that is codon optimized for expression in bacteria.

In some embodiments, the cell is a eukaryotic cell, optionally a fungal cell, a yeast cell, an insect cell, a plant cell or a mammalian cell.

In some embodiments, one or more of the genes encoding TAL, 4CL, CHS, and/or CHI are expressed on plasmids. In other embodiments, one or more of the genes encoding TAL, 4CL, CHS, and/or CHI are integrated into the genome of the cell.

In some embodiments, the production of naringenin is increased by protein engineering of the TAL, 4CL, CHS, and/or CHI in the cell. In some embodiments, the production of naringenin is increased by balancing expression of the genes encoding TAL, 4CL, CHS and CHI in the cell, optionally by selecting promoters of various strengths to drive expression of the genes encoding TAL, 4CL, CHS and CHI.

In some embodiments, the cell further comprises a recombinantly-expressed malonate assimilation pathway; optionally the recombinantly-expressed malonate assimilation pathway comprises genes encoding MatB and MatC, for example from *Rhizobium trifolii*.

In some embodiments, the cell further comprises simultaneous deletions of genes sdhA, adhE, brnQ, and citE and overexpresses the enzymes acetyl-CoA synthase, acetyl-CoA carboxylase, biotin ligase, and pantothenate kinase.

In some embodiments, upon culturing the cell produces at least about 500 micrograms/liter naringenin in the culture medium.

According to certain aspects of the invention, methods for producing one or more flavonoids or naringenin are provided. The methods include culturing the cells described herein to produce the one or more flavonoids or the naringenin. In some embodiments, the methods further include recovering the one or more flavonoids or the naringenin from the culture medium or the cells. In some embodiments, the culture has a carbon source and the carbon source is glucose or a glucose polymer. In some embodiments, the culture medium is not supplemented with a precursor of naringenin synthesis. In some embodiments, the precursor of naringenin synthesis is tyrosine or p-coumaric acid.

In some embodiments, the cells are cultured in the presence of the fatty acid pathway inhibitor cerulenin. In embodiments in which the cells recombinantly-express a malonate assimilation pathway including genes encoding MatB and MatC, for example from *Rhizobium trifolii*, the cell culture optionally is supplemented with malonate.

In some embodiments, the cells produce at least about 500 micrograms/liter naringenin in the culture medium.

According to certain aspects of the invention, genetically modified microorganisms are provided that include one or more recombinant nucleic acid molecules encoding tyrosine ammonia lyase (TAL), 4-coumarate:CoA ligase (4CL), chalcone synthase (CHS), and chalcone isomerase (CHI).

According to certain aspects of the invention, methods for producing one or more flavonoids or naringenin are provided. The method include genetically modifying a cell to recombinantly express at least one of: tyrosine ammonia lyase (TAL), 4-coumarate:CoA ligase (4CL), chalcone synthase (CHS), and chalcone isomerase (CHI), culturing a population of said cells, and optionally collecting the one or more flavonoids or naringenin from the culture medium or the population of cells that have been genetically modified to produce one or more flavonoids or naringenin.

In some embodiments, the gene encoding TAL is a yeast gene or a bacterial gene, optionally a *Rhodotorula glutinis* gene or a *Rhodobacter sphaeroides* gene. In some embodiments, the gene encoding 4CL is a plant gene or a bacterial gene, optionally a *Petroselinum crispus* gene or a *Streptomyces coelicolor* gene. In some embodiments, the gene encoding CHS and/or the gene encoding CHI is a plant gene, optionally a *Petunia hybrida* gene or an *Arabidopsis thaliana* gene. In some embodiments, the gene encoding CHI is a *Medicago sativa* gene or a *Pueraria lobata* gene.

In some embodiments, the genes encoding TAL, 4CL, CHS, and/or CHI are expressed from a single polycistronic operon, or wherein each of the genes is expressed from a separate promoter. Optionally, one or more of the separate promoters is a trc promoter, a T7 promoter, or a constitutive promoter, optionally $P_{GAP}$.

In some embodiments, the cell is a prokaryotic cell, and optionally the cell is a strain previously engineered for high endogenous L-tyrosine production or p-coumaric acid synthesis. Preferably the endogenous L-tyrosine production is at least about 250 milligrams/liter. Examples of strains that produce high levels of L-tyrosine or that are engineered for high endogenous L-tyrosine production include the P2 and rpoA14$^R$ strains described herein.

In some embodiments, the cell is a bacterial cell, optionally an *E. coli* cell. In some embodiments, one or more of the genes encoding TAL, 4CL, CHS, and/or CHI is a synthetic gene that is codon optimized for expression in bacteria.

In some embodiments, the cell is a eukaryotic cell, optionally a fungal cell, a yeast cell, an insect cell, a plant cell or a mammalian cell.

In some embodiments, one or more of the genes encoding TAL, 4CL, CHS, and/or CHI are expressed on plasmids. In other embodiments, one or more of the genes encoding TAL, 4CL, CHS, and/or CHI are integrated into the genome of the cell.

In some embodiments, the production of naringenin is increased by protein engineering of the TAL, 4CL, CHS, and/or CHI in the cell. In some embodiments, the production of naringenin is increased by balancing expression of the genes encoding TAL, 4CL, CHS and CHI in the cell, optionally by selecting promoters of various strengths to drive expression of the genes encoding TAL, 4CL, CHS and CHI.

In some embodiments, the cell further comprises a recombinantly-expressed malonate assimilation pathway; optionally the recombinantly-expressed malonate assimilation pathway comprises genes encoding MatB and MatC, such as from *Rhizobium trifolii*. In embodiments in which the cells recombinantly-express a malonate assimilation pathway, the cell culture optionally is supplemented with malonate.

In some embodiments, the cell further comprises simultaneous deletions of genes sdhA, adhE, brnQ, and citE and overexpresses the enzymes acetyl-CoA synthase, acetyl-CoA carboxylase, biotin ligase, and pantothenate kinase.

In some embodiments, the carbon source is glucose or a glucose polymer. In some embodiments, the culture medium is not supplemented with a precursor of naringenin synthesis. In some embodiments, the precursor of naringenin synthesis is tyrosine or p-coumaric acid. In some embodiments, the cells are cultured in the presence of the fatty acid pathway inhibitor cerulenin.

In some embodiments, the cells produce at least about 500 micrograms/liter naringenin in the culture medium.

According to certain aspects of the invention, isolated nucleic acid molecules are provided, selected from the group consisting of:

(a) an isolated nucleic acid molecule comprising SEQ ID NO:30, SEQ ID NO:32, or SEQ ID NO:34; or (b) an isolated nucleic acid molecule that is a reverse complement of the full-length sequence of (a).

According to certain aspects of the invention, recombinant expression vectors are provided that include one or more of the nucleic acid molecules described herein operably linked to one or more promoters.

According to certain aspects of the invention, cells are provided that include a recombinant expression vector described herein. In some embodiments, the cell is a bacterial cell, a fungal cell, a yeast cell, a plant cell, an insect cell or an animal cell.

According to certain aspects of the invention, methods for the production of naringenin are provided that include culturing the cells described herein under conditions that permit production of naringenin. In some embodiments, the methods further include recovering the naringenin from the culture medium or the cell.

These and other aspects of the invention are described further below.

DETAILED DESCRIPTION OF THE INVENTION

Flavonoids comprise a highly diverse family of plant secondary polyphenols which possess biochemical properties (estrogenic, antioxidant, antiviral, antibacterial, antiobesity, and anticancer) that are useful for the treatment of several human pathologies [1-5]. Despite this broad range of pharmaceutical indications, however, their widespread use and availability are currently limited by inefficiencies in both their chemical synthesis and extraction from natural plant sources. As a result, the development of strains and processes for the microbial production of flavonoids has emerged recently as an interesting and commercially-attractive challenge for metabolic engineering.

Figure 1:
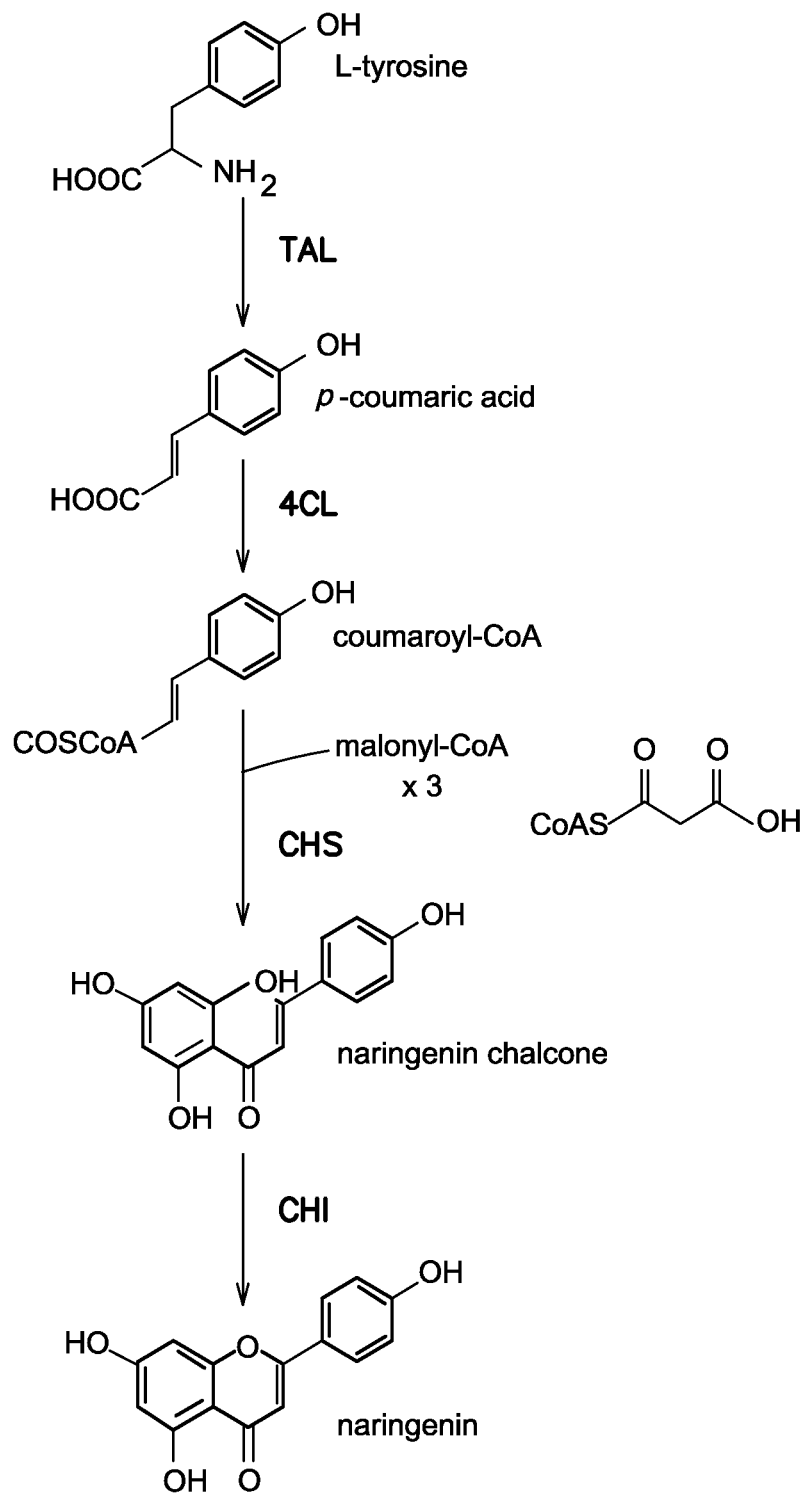
FIG. 1 shows an early phenylpropanoid pathway for the conversion of L-tyrosine to naringenin. Four heterologous enzymes must be expressed in *E. coli* to mediate the synthesis of naringenin from L-tyrosine: tyrosine ammonia lyase (TAL), 4-coumarate:CoA ligase (4CL), chalcone synthase (CHS), and chalcone isomerase (CHI).

Although a myriad of enzymes are involved with structural diversification, only four catalytic steps are required for the conversion of the aromatic amino acid L-tyrosine to the main flavanone precursor, naringenin (FIG. 1). This process begins with the conversion of L-tyrosine to the phenylpropanoic acid p-coumaric acid through the action of the enzyme tyrosine ammonia lyase (TAL). Once p-coumaric acid has been generated, 4-coumarate:CoA ligase (4CL) then mediates the formation of its corresponding CoA ester, coumaroyl-CoA. This compound is subsequently condensed with three malonyl-CoA units by the sequential action of the type III polyketide synthase, chalcone synthase (CHS), and, in the final step, the resulting naringenin chalcone is stereospecifically isomerized by chalcone isomerase (CHI) to form the (2S)-flavanone naringenin. This compound provides the basis for a variety of other flavonoid molecules which are created through the combined actions of functionalizing enzymes which hydroxylate, reduce, alkylate, oxidize, and glucosylate this phenylpropanoid core structure [2, 6].

Although previous studies have already made significant gains in demonstrating the feasibility of microbial naringenin production in *Escherichia coli*, the established protocols suffer from two severe disadvantages that could be prohibitive during process scale-up [7-9]. The first main shortcoming is that fermentation protocols often require two separate cultivation steps to achieve high flavonoid titers. Typically, strains are first grown in rich media in order to generate biomass and ensure adequate heterologous protein expression. After reaching a target density, cells are then collected and transferred to minimal media for the second stage of the process during which flavonoids are produced from supplemented phenylpropanoic precursors. While the separation of biomass can be performed relatively easily on a laboratory scale, such procedures are significantly more difficult and expensive when translated to large-scale fermentation processes. As such, the development of robust strains that can perform equally well in a single medium formulation is absolutely required for this process.

The second major drawback found in these studies is the heavy reliance on precursor feeding (typically L-tyrosine or p-coumaric acid) to achieve high levels of flavonoid production. This requirement is particularly unfavorable for the case of p-coumaric acid supplementation, given its high market price, especially in comparison to both L-tyrosine and glucose (Table 1). Thus, there is an obvious economic incentive to develop strains capable of converting cheaper feedstocks such as glucose to these high value flavonoid compounds. When compared on a gram per gram basis, such an accomplishment would represent a 646-fold increase in product value, a significant leap compared to the meager 2.4-fold increase seen with p-coumaric acid feeding.

In this study, we outline the construction and evaluation of a series of strains capable of circumventing both of these critical limitations. To mediate the production of naringenin from glucose, a four-enzyme heterologous pathway (consisting of TAL, 4CL, CHS, and CHI) was assembled within two strains which have been previously engineered for high L-tyrosine production [10]. Due to the incredible sensitivity of strain performance on both enzyme source and relative gene expression levels, sequential optimization was required for each step of the pathway. However, once an optimum metabolic balance had been achieved, the resulting strains were found to possess a remarkably robust constitution, exhibiting unfettered growth and competitive naringenin titers (up to 84 mg/l with the addition of cerulenin), even with a single-stage fermentation in minimal media.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Pathways are described that have been designed and implemented to produce the flavonoid precursor naringenin from glucose through recombinant expression of tyrosine ammonia lyase (TAL), 4-coumarate:CoA ligase (4CL), chalcone synthase (CHS), and chalcone isomerase (CHI). This pathway represents an unexpectedly efficient new system for producing the flavonoid precursor naringenin, as well as intermediate products of the novel pathway.

The pathways described herein for the production of flavonoids and flavonoid precursors in cells involve several enzymatic components. In some embodiments, the gene encoding TAL is a yeast gene or a bacterial gene, such as a *Rhodotorula glutinis* gene or a *Rhodobacter sphaeroides* gene. In some embodiments, the gene encoding 4CL is a plant gene or a bacterial gene, such as a *Petroselinum crispus* gene or a *Streptomyces coelicolor* gene. In some embodiments, the gene encoding CHS and/or the gene encoding CHI is a plant gene, such as a *Petunia hybrida* gene or an *Arabidopsis thaliana* gene. In some embodiments, the gene encoding CHI is a plant gene, such as a *Medicago sativa* gene or a *Pueraria lobata* gene. It should be appreciated that some cells compatible with the invention may express an endogenous copy of one of more of the aforementioned enzymatic components as well as a recombinant copy.

As one of ordinary skill in the art would be aware, homologous genes for these enzymes can be obtained from other species and can be identified by homology searches, for example through a protein BLAST search, available at the National Center for Biotechnology Information (NCBI) internet site. Genes associated with the invention can be cloned, for example by PCR amplification and/or restriction digestion, from DNA from any source of DNA which contains the given gene. In some embodiments, a gene associated with the invention is synthetic. Any means of obtaining a gene encoding for an enzyme associated with the invention is compatible with the instant invention.

Aspects of the invention include strategies to optimize production of the flavonoid precursor naringenin from a cell. Optimized production of naringenin refers to producing a higher amount of naringenin following pursuit of an optimization strategy than would be achieved in the absence of such a strategy. Optimization of production of naringenin can involve modifying a gene encoding for an enzyme before it is recombinantly expressed in a cell. In some embodiments, such a modification involves codon optimization for expression in a bacterial cell. Codon usages for a variety of organisms can be accessed in the Codon Usage Database (kazusa.or.jp/codon/). Codon optimization, including identification of optimal codons for a variety of organisms, and methods for achieving codon optimization, are familiar to one of ordinary skill in the art, and can be achieved using standard methods.

In some embodiments, modifying a gene encoding for an enzyme before it is recombinantly expressed in a cell involves making one or more mutations in the gene encoding for the enzyme before it is recombinantly expressed in a cell. For example, a mutation can involve a substitution or deletion of a single nucleotide or multiple nucleotides. In some embodiments, a mutation of one or more nucleotides in a gene encoding for an enzyme will result in a mutation in the enzyme, such as a substitution or deletion of one or more amino acids.

Additional changes can include increasing copy numbers of the components of pathways active in production of naringenin or a flavonoid, such as by additional episomal expression. In some embodiments, screening for mutations in components of the production of naringenin or a flavonoid, or components of other pathways, that lead to enhanced production of naringenin or a flavonoid may be conducted through a random mutagenesis screen, or through screening of known mutations. In some embodiments, shotgun cloning of genomic fragments could be used to identify genomic regions that lead to an increase in production of naringenin or a flavonoid, through screening cells or organisms that have these fragments for increased production of naringenin or a flavonoid. In some cases one or more mutations may be combined in the same cell or organism.

In some embodiments, production of naringenin or a flavonoid in a cell can be increased through manipulation of enzymes that act in the same pathway as the enzymes associated with the invention. For example, in some embodiments it may be advantageous to increase expression of an enzyme or other factor that acts upstream or downstream of a target enzyme such as an enzyme associated with the invention. This could be achieved by over-expressing the upstream or downstream factor using any standard method.

A further strategy for optimization of production of naringenin or a flavonoid is to increase expression levels of one or more genes associated with the invention, which can be described as "pathway balancing". This may be accomplished, for example, through selection of appropriate promoters and ribosome binding sites. In some embodiments, the production of naringenin or a flavonoid is increased by balancing expression of the genes encoding TAL, 4CL, CHS and CHI in the cell, such as by selecting promoters of various strengths to drive expression of the genes encoding TAL, 4CL, CHS and CHI. In some embodiments, this may include the selection of high-copy number plasmids, or low or medium-copy number plasmids. The step of transcription termination can also be targeted for regulation of gene expression, through the introduction or elimination of structures such as stem-loops.

The production of naringenin or a flavonoid requires incorporation of three malonyl-CoA molecules per molecule of naringenin or a flavonoid. Thus the supply of malonyl-CoA can be a limiting factor in production of naringenin or a flavonoid, and accordingly increasing the supply of malonyl-CoA is preferred in order to increase production of naringenin or a flavonoid. This can be accomplished in several ways, including those described in the literature (see, for example, references [7-9, 18]), each of which is contemplated to be used in combination with the other features described herein for increasing production of naringenin or a flavonoid. For example, the cells described herein may further include simultaneous deletions of genes sdhA, adhE, brnQ, and citE and overexpresses the enzymes acetyl-CoA synthase, acetyl-CoA carboxylase, biotin ligase, and pantothenate kinase, as described in [18].

Thus in some embodiments, the cell further comprises a recombinantly-expressed malonate assimilation pathway. For example, a malonate assimilation pathway including genes encoding MatB and MatC (such as from *Rhizobium trifolii*) can be recombinantly expressed in the cells expressing the genes encoding TAL, 4CL, CHS and CHI. The expression of the recombinant malonate assimilation pathway provides both the transport of supplemented malonate into the cell, as well as its subsequent conversion to malonyl-CoA.

The cells described herein and used in the methods described herein can be a strain that produces high titers of L-tyrosine or a strain previously engineered for high endogenous L-tyrosine production or p-coumaric acid synthesis. Examples of strains that produce high titers of L-tyrosine or that are engineered for high endogenous L-tyrosine production include the P2 and rpoA14$^R$ strains described herein (see also U.S. provisional application Ser. No. 61/332,560, filed May 7, 2010, entitled "Mutations And Genetic Targets For Enhanced L-Tyrosine Production," applicants Christine Santos and Gregory Stephanopoulos). In some embodiments the endogenous L-tyrosine production (titer) is at least about 250 milligrams/liter (mg $L^{-1}$). For example the titer may be at least about 250, 300, 350, 400, 450, 500, 550, 600, 650, 700, 750, 800, 850, 900, 950, 1000, 1050, 1100, 1150, 1200, 1300, 1400, 1500, 1600, 1700, 1800, 1900, 2000 or more than 2000 mg $L^{-1}$ including any intermediate values. Even higher titers include gram per liter (g $L^{-1}$) titers, for example, titers of at least about 2.5, 3.0, 3.5, 4.0, 4.5, 5.0, 5.5, 6.0, 7.0, 8.0, 9.0, 10.0, 11.0, 12.0, 13.0, 14.0, 15.0 or more g $L^{-1}$ including any intermediate values.

In other embodiments, the fatty acid pathway is inhibited in order to reduce the amount of malonyl-CoA used for fatty acid synthesis by the cells expressing the genes encoding TAL, 4CL, CHS and CHI. For example, the cells can be contacted with the fatty acid pathway inhibitor cerulenin, which represses both fabB and fabF, thus limiting the amount of malonyl-CoA lost to the synthesis of fatty acids.

The invention also encompasses isolated polypeptides containing mutations or codon optimizations in residues described herein, and isolated nucleic acid molecules encoding such polypeptides. As used herein, the terms "protein" and "polypeptide" are used interchangeably and thus the term polypeptide may be used to refer to a full-length polypeptide and may also be used to refer to a fragment of a full-length polypeptide. As used herein with respect to polypeptides, proteins, or fragments thereof, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may be, but need not be, substantially pure. The term "substantially pure" means that the proteins or polypeptides are essentially free of other substances with which they may be found in production, nature, or in vivo systems to an extent practical and appropriate for their intended use. Substantially pure polypeptides may be obtained naturally or produced using methods described herein and may be purified with techniques well known in the art. Because an isolated protein may be admixed with other components in a preparation, the protein may comprise only a small percentage by weight of the preparation. The protein is nonetheless isolated in that it has been separated from the substances with which it may be associated in living systems, i.e. isolated from other proteins.

The invention also encompasses nucleic acids that encode for any of the polypeptides described herein, libraries that contain any of the nucleic acids and/or polypeptides described herein, and compositions that contain any of the nucleic acids and/or polypeptides described herein. It should be appreciated that libraries containing nucleic acids or proteins can be generated using methods known in the art. A library containing nucleic acids can contain fragments of genes and/or full-length genes and can contain wild-type sequences and mutated sequences. A library containing proteins can contain fragments of proteins and/or full length proteins and can contain wild-type sequences and mutated sequences. It should be appreciated that the invention encompasses codon-optimized forms of any of the nucleic acid and protein sequences described herein.

The invention encompasses any type of cell that recombinantly expresses genes associated with the invention, including prokaryotic and eukaryotic cells. In some embodiments the cell is a bacterial cell, such as *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp. and *Pantoea* spp. The bacterial cell can be a Gram-negative cell such as an *Escherichia coli* (*E. coli*) cell, or a Gram-positive cell such as a species of *Bacillus*. In other embodiments, the cell is a fungal cell such as a yeast cell, e.g., *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp. and industrial polyploid yeast strains. Preferably the yeast strain is a *S. cerevisiae* strain. Other examples of fungi include *Aspergillus* spp., *Pennicilium* spp., *Fusarium* spp., *Rhizopus* spp., *Acremonium* spp., *Neurospora* spp., *Sordaria* spp., *Magnaporthe* spp., *Allomyces* spp., *Ustilago* spp., *Botrytis* spp., and *Trichoderma* spp. In other embodiments, the cell is an algal cell, or a plant cell.

It should be appreciated that some cells compatible with the invention may express an endogenous copy of one or more of the genes associated with the invention as well as a recombinant copy. In some embodiments, if a cell has an endogenous copy of one or more of the genes associated with the invention then the methods will not necessarily require adding a recombinant copy of the gene(s) that are endogenously expressed. In some embodiments the cell may endogenously express one or more enzymes from the pathways described herein and may recombinantly express one or more other enzymes from the pathways described herein for efficient production of naringenin or a flavonoid.

In some embodiments, one or more of the genes associated with the invention is expressed in a recombinant expression vector. As used herein, a "vector" may be any of a number of nucleic acids into which a desired sequence or sequences may be inserted by restriction and ligation for transport between different genetic environments or for expression in a host cell. Vectors are typically composed of DNA, although RNA vectors are also available. Vectors include, but are not limited to: plasmids, fosmids, phagemids, virus genomes and artificial chromosomes.

A cloning vector is one which is able to replicate autonomously or integrated in the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host cell such as a host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

When the nucleic acid molecule that encodes any of the enzymes of the claimed invention is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA). That heterologous DNA (RNA) is placed under operable control of transcriptional elements to permit the expression of the heterologous DNA in the host cell. Heterologous expression of genes associated with the invention, for production of naringenin or a flavonoid, is demonstrated in the Examples using *E. coli*. The novel method for producing naringenin or a flavonoid can also be expressed in other bacterial cells, fungi (including yeast cells), plant cells, etc.

A nucleic acid molecule that encodes the enzyme of the claimed invention can be introduced into a cell or cells using methods and techniques that are standard in the art. For example, nucleic acid molecules can be introduced by standard protocols such as transformation including chemical transformation and electroporation, transduction, particle bombardment, etc. Expressing the nucleic acid molecule encoding the enzymes of the claimed invention also may be accomplished by integrating the nucleic acid molecule into the genome.

In some embodiments one or more genes associated with the invention is expressed recombinantly in a bacterial cell. Bacterial cells according to the invention can be cultured in media of any type (rich or minimal) and any composition. As would be understood by one of ordinary skill in the art, routine optimization would allow for use of a variety of types of media. The selected medium can be supplemented with various additional components. Some non-limiting examples of supplemental components include glucose, antibiotics, IPTG for gene induction, ATCC Trace Mineral Supplement, malonate, cerulenin and glycolate. Similarly, other aspects of the medium, and growth conditions of the cells of the invention may be optimized through routine experimentation. For example, pH and temperature are non-limiting examples of factors which can be optimized. In some embodiments, factors such as choice of media, media supplements, and temperature can influence production levels of naringenin or a flavonoid. In some embodiments the concentration and amount of a supplemental component may be optimized. In some embodiments, how often the media is supplemented with one or more supplemental components, and the amount of time that the media is cultured before harvesting naringenin or a flavonoid, is optimized.

In some embodiments the temperature of the culture may be between 25 and 40 degrees. For example it may be 25, 26, 27, 28, 29, 30, 31, 32, 33, 34, 35, 36, 37, 38, 39 or 40 degrees, or any value in between. In certain embodiments the temperature is between 30 and 32 degrees including 30, 31 and 32 and any value in between. As would be understood by one of ordinary skill in the art, the optimal temperature in which to culture a cell for production of naringenin or a flavonoid may be influenced by many factors including the type of cell, the growth media and the growth conditions.

Other non-limiting factors that can be varied through routine experimentation in order to optimize production of naringenin or a flavonoid include the concentration and amount of feedstock and any supplements provided, how often the media is supplemented, and the amount of time that the media is cultured before harvesting the naringenin or flavonoid. In some embodiments the cells may be cultured for 6, 12, 18, 24, 30, 36, 42, 45, 50, 55, 60, 65, 70, 75, 80, 85, 90, 95, 100, 110, 120, 130, 140, 150, 160 or greater than 160 hours, including all intermediate values. In some embodiments optimal production is achieved after culturing the cells for several days such as 3-4 days. However it should be appreciated that it would be routine experimentation to vary and optimize the above-mentioned parameters and other such similar parameters.

According to aspects of the invention, high titers of naringenin are produced through the recombinant expression of genes associated with the invention, in a cell. As used herein "high titer" refers to a titer in the milligrams per liter (mg $L^{-1}$) scale. The titer produced for a given product will be influenced by multiple factors including choice of media. In some embodiments the total naringenin titer is at least 0.5 mg $L^{-1}$ (500 micrograms per liter). For example the titer may be 0.5, 0.6, 0.7, 0.8, 0.9, 1.0, 1.1, 1.2, 1.3, 1.4, 1.5, 2.0, 2.5, 3.0, 3.5, 4.0, 4.5, 5.0, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100 or more than 100 mg $L^{-1}$ including any intermediate values.

The liquid cultures used to grow cells associated with the invention can be housed in any of the culture vessels known and used in the art. In some embodiments large scale production in an aerated reaction vessel such as a stirred tank reactor can be used to produce large quantities of naringenin, which can be recovered from the cell culture.

EXAMPLES

Materials and Methods

Construction of (DE3) Lysogenic Strains for T7 Expression

The λDE3 Lysogenization Kit (EMD Chemicals) was used to prepare strains *E. coli* K12, P2, and rpoA14$^R$ for the expression of genes cloned in T7 expression vectors. Manufacturer's protocols were followed for lysogenization and strain verification. Strains that have undergone λDE3 lysogenization are indicated by the "(DE3)" notation following their names.

Codon Optimization and Synthesis of TAL, 4CL, and CHI

CHI from *Pueraria lobata* (PlCHI) was codon optimized for *E. coli* expression and synthesized using established protocols for gene synthesis [11]. Oligonucleotides were designed with the software package Gene Morphing System (GeMS), which was previously available for public use [12]. Following assembly, the synthesized chi gene was cloned into pTrcHis2B (Invitrogen) using the primers CS420 CHI sense KpnI and CS421 CHI anti HindIII (Table 2) and the restriction enzymes KpnI and HindIII. Errors found within the resulting plasmid, pTrc-PlCHI$^{syn}$, were corrected with the QuikChange Multi Site-Directed Mutagenesis Kit (Stratagene) using the manufacturer's protocols. Codon optimization and synthesis of both *Rhodotorula glutinis* tal (RgTAL) and *Petroselinum crispus* (parsley) 4CL-1 (Pc4CL) were performed by DNA2.0. In future references, synthetic genes/proteins are denoted by a superscript "syn." The DNA sequences and corresponding amino acids for all synthesized genes are provided in Supplementary Table S1.

Heterologous Pathway Construction and Assembly

All constructed plasmids described below were verified by colony PCR and sequencing. Routine transformations were performed with chemically competent *E. coli* DH5α cells (Invitrogen) according to the manufacturer's protocols. A list of plasmids and strains used in this study can be found in Table 3.

Construction of pCS204

The pCS204 flavonoid plasmid contains *Rhodobacter sphaeroides* tal (RsTAL, also known as hutH), *Streptomyces coelicolor* 4c1-2 (Sc4CL), *Arabidopsis thaliana* chs (AtCHS), and synthetic *P. lobata* chi (PlCHI$^{syn}$), each under the control of an independent trc promoter. The plasmid was assembled by a three-step cloning process. Briefly, the first three genes were first independently cloned into pTrcHis2B or pTrcsGFP (pTrcHis2B carrying a codon-optimized superfolder green fluorescent protein [13]) (C. Santos, unpublished) using primers CS313-CS318, CS420-CS421, and the restriction enzyme pairs specified in Table 2 to form pTrc-RsTAL, pTrc-Sc4CL, and pTrc-AtCHS. *R. sphaeroides* genomic DNA was used as a template for amplification of RsTAL and was obtained from American Type Culture Collection (ATCC 17023). Similarly, *S. coelicolor* genomic DNA was used as a template for Sc4CL and was extracted using the Wizard Genomic DNA Kit (Promega). AtCHS was amplified from an *A. thaliana* cDNA library from American Type Culture Collection (pFL61, ATCC 77500).

In the second round of cloning, the $P_{trc}$-Sc4CL and $P_{trc}$-PlCHI$^{syn}$ regions were amplified from their respective plasmids with primers CS481-CS485 and cloned into pTrc-RsTAL and pTrc-AtCHS with the restriction sites HindIII and BstBI, respectively. It is noteworthy to mention that $P_{trc}$-PlCHI$^{syn}$ was amplified with two rounds of PCR (using the primer pairings CS483-CS484 and CS483-CS485) in order to incorporate a multi-cloning site designed to facilitate the addition of future genes/elements within this plasmid. The resulting plasmids from this second round of cloning were named pTrc-RsTAL-Sc4CL and pTrc-AtCHS-PlCHI$^{syn}$.

In the third and final round of assembly, $P_{trc}$-AtCHS-$P_{trc}$-PlCHI was amplified from pTrc-AtCHS-PlCHI with primers CS486 CHS-CHI sense BamHI and CS487 CHS-CHI anti BamHI. This fragment was then cloned into pTrc-RsTAL-Sc4CL with restriction enzyme BamHI to form plasmid pCS204.

Gene sequences and orientations were verified by colony PCR and sequencing after each round of cloning.

TAL/4CL Plasmid Variants pJ206-RgTAL$^{syn}$ (from DNA2.0) and pTrcHis2B were digested with restriction enzymes NcoI and HindIII, and the appropriate fragments were ligated to form pTrc-RgTAL$^{syn}$. pTrc-RgTAL$^{syn}$-Sc4CL was subsequently constructed by amplifying $P_{trc}$-Sc4CL with primers CS481 pTrc 4CL sense and CS482 pTrc 4CL anti (Table 2) and cloning the resulting product into the HindIII site of pTrc-RgTAL$^{syn}$. pTrc-RgTAL$^{syn}$-Pc4CL$^{syn}$ was assembled by digestion of both pJ281-Pc4CL$^{syn}$ (from DNA2.0) and pTrc-RgTAL$^{syn}$ with SalI followed by ligation of the appropriate fragments.

pET-RgTAL$^{syn}$ was constructed by amplifying RgTAL$^{syn}$ from pTrc-RgTAL$^{syn}$ using primers CS619 tal sense NcoI and CS620 tal anti SalI (Table 2) and cloning the resulting product into the NcoI/SalI sites of pETDuet-1 (Novagen). Because subsequent insertion of Pc4CL$^{syn}$ into this plasmid required the restriction site NdeI, the QuikChange Multi Site-Directed Mutagenesis Kit (Stratagene) and primer CS657 pETtal (Quikchange) were used to change an internal NdeI sequence (within RgTAL$^{syn}$) from CA<u>T</u>ATG to CA<u>C</u>ATG. Pc4CL$^{syn}$ was subsequently cloned into this plasmid through amplification from pJ281-Pc4CL$^{syn}$ with primers CS621 4CL sense NdeI and CS622 4CL anti AvrII followed by insertion into the NdeI/AvrII sites of pET-RgTAL$^{syn}$. The resulting plasmid was named pET-RgTAL$^{syn}$-Pc4CL$^{syn}$.

pCDF-RgTAL$^{syn}$-Pc4CL$^{syn}$ was constructed through the digestion of both pET-RgTAL$^{syn}$-Pc4CL$^{syn}$ and pCDFDuet-1 (Novagen) with NcoI and AvrII, followed by ligation of the appropriate fragments. pCDF-trc-RgTAL$^{syn}$-Pc4CL$^{syn}$ was constructed by amplifying $P_{trc}$-RgTAL$^{syn}$-$P_{trc}$-Pc4CL$^{syn}$ from pTrc-RgTAL$^{syn}$-Pc4CL$^{syn}$ using primers CS786 tal sense FseI and CS787 rrnB anti BamHI (Table 2). FseI/BamHI-digested products were then ligated with a similarly digested pCDFDuet-1 plasmid.

To assemble pACYC-Sc4CL, the $P_{trc}$-Sc4CL cassette was first amplified with primers CS481 pTrc 4CL sense and CS482 pTrc 4CL anti (Table 2), then cloned into the HindIII restriction site of pACY184.

CHS/CHI Plasmid Variants pACKm-AtCHS-PlCHI$^{syn}$ was constructed by amplifying the lacI-$P_{trc}$-AtCHS-$P_{trc}$-PlCHI$^{syn}$ region from pTrc-AtCHS-PlCHI using primers CS644 lacI sense AatII and CS645 CHI anti BsiWI (Table 2). The resulting product was subsequently cloned into the plasmid pACKm-FLP-Trc-MEP (P. Ajikumar, unpublished) using the AatII and BsiWI restriction sites.

pCDF-AtCHS was constructed by amplifying AtCHS from pTrc-AtCHS using primers CS627 CHS sense NdeI and CS628 CHS anti AvrII (Table 2) and cloning this PCR product into pCDFDuet-1 with the restriction sites/enzymes NdeI and AvrII. To assemble, pCDF-AtCHS-PlCHI$^{syn}$, PlCHI$^{syn}$ was amplified with primers CS629 CHI sense NcoI and CS630 CHI anti NotI using pTrc-PlCHI$^{syn}$ as a template and cloned into pCDF-AtCHS with the sites NcoI and NotI.

pOM-PhCHS-MsCHI was constructed by digesting pOM-PhCHS-MsCHI-At4CL (R. Lim, unpublished) with BsrGI and BglII, followed by ligation with oligos CS792 BsrGI-BglII oligo 1 and CS793 BsrGI-BglII oligo 2 (Table 2) (at a ratio of 215 ng oligo per 100 ng digested plasmid).

Cultivation Conditions

Two different fermentation protocols were developed for evaluating a strain's potential for flavonoid production. The first approach involved the cultivation of strains in 50 ml medium with 250-300 rpm orbital shaking at a temperature of 30° C. Induction of heterologous pathway expression was performed either at the beginning of the culture or during mid-exponential phase (as indicated for each experiment), and flavonoid production was assayed after 72 hr. In the second fermentation scheme, strains were first cultured in 25 ml medium at 37° C. with 250-300 rpm orbital shaking. After a period of 15-24 hr (or after an $OD_{600}$ of 1.0-2.0 had been reached), an additional 25 ml fresh medium was provided, pathway expression was induced, and cultures were subsequently transferred to a lower temperature (30° C.) for optimal enzyme synthesis and flavonoid production. Flavonoid concentrations were measured after a total fermentation time of 48 hr.

All liquid cultivations were conducted in MOPS minimal medium (Teknova) [14] cultures supplemented with 5 g/l glucose and an additional 4 g/l $NH_4Cl$. When appropriate, antibiotics were added in the following concentrations: 100 μg/ml carbenicillin for the maintenance of pTrc- or pET-derived plasmids, 34 μg/ml chloramphenicol for pHACM-derived plasmids, 68 μg/ml chloramphenicol for pACYC-derived plasmids and pRARE2 (Novagen), and 20 μg/ml kanamycin for pACKm-derived plasmids. Isopropyl-β-D-thiogalactopyranoside (IPTG, EMD Chemicals) was provided at a concentration of 1 mM for the induction of expression from both trc and T7 promoters. Cultures for L-phenylalanine auxotrophic (ΔpheA) strains were additionally supplemented with L-phenylalanine (Sigma) at a concentration of 0.35 mM. For malonyl CoA availability experiments, cerulenin (Cayman Chemicals) and sodium malonate dibasic (Sigma) were added at a concentration 20 μg/ml and 2 g/l (1 g/l added twice), respectively.

Analytical Methods

For the quantification of L-tyrosine, cell-free culture supernatants were filtered through 0.2 μm PTFE membrane syringe filters (VWR International) and used for HPLC analysis with a Waters 2690 Separations module connected with a Waters 996 Photodiode Array detector (Waters) set to a wavelength of 278 nm. The samples were separated on a Waters Resolve C18 column with 0.1% (vol/vol) trifluoroacetic acid (TFA) in water (solvent A) and 0.1% (vol/vol) TFA in acetonitrile (solvent B) as the mobile phase. The following gradient was used at a flow rate of 1 ml/min: 0 min, 95% solvent A+5% solvent B; 8 min, 20% solvent A+80% solvent B; 10 min, 80% solvent A+20% solvent B; 11 min, 95% solvent A+5% solvent B.

To quantify levels of p-coumaric acid, cinnamic acid, and naringenin, 1 ml of culture supernatant was first extracted with an equal volume of ethyl acetate (EMD Chemicals). After vortexing and centrifugation, the top organic layer was separated and evaporated to dryness, and the remaining residue was resolubilized with 200 μl methanol (EMD Chemicals). Samples were analyzed using a Shimadzu Prominence HPLC system and a Waters Resolve C18 column using the same buffer system described above. Specifically, flavonoid compounds were separated with the following acetonitrile/water gradient at a flow rate of 1 ml/min: 0 min, 90% solvent A+10% solvent B; 10 min, 60% solvent A+40% solvent B; 15 min, 60% solvent A+40% solvent B; 17 min, 90% solvent A+10% solvent B. Products were detected by monitoring their absorbance at 250 nm (p-coumaric acid) and 312 nm (cinnamic acid, naringenin), and concentrations were determined through the use of the corresponding chemical standards (Sigma).

Cell densities of cultures were determined by measuring their absorbance at 600 nm with an Ultrospec 2100 pro UV/Visible spectrophotometer (Amersham Biosciences).

Results

Because L-tyrosine serves as the main precursor for the flavonoid naringenin, strains exhibiting an enhanced capacity for its synthesis [10] provide a natural platform for exploring the potential of microbial flavonoid production from glucose. With a high flux through the aromatic amino acid pathway already in place, the next logical step towards this goal then becomes the assembly and grafting of an appropriate flavonoid biosynthetic gene cluster within these specific strain backgrounds. In this study, our main objective was to engineer a functional pathway consisting of TAL, 4CL, CHS, and CHI in order to mediate this conversion of L-tyrosine to naringenin.

Selection of Enzyme Sources

Unfortunately, selecting specific enzyme sources can be a particularly thorny task due to inherent difficulties in predicting heterologous enzyme expression and activity. Consequently, to increase our chances for success, we opted to construct a four-gene assembly comprised solely of variants that have previously been shown to be functional and active for other similar applications. For the first step of the phenylpropanoid pathway, we chose a well-characterized TAL variant from R. sphaeroides that exhibited a 90 to 160-fold higher catalytic efficiency for L-tyrosine over L-phenylalanine [15, 16]. Since most TAL enzymes exhibit some level of activity on both amino acids, it was important to select a form with a strong preference for L-tyrosine in order to ensure maximal substrate utilization within our strains. For the second catalytic step, 4CL-2 from S. coelicolor was selected due to its unique ability to convert both p-coumaric acid and cinnamic acid into their corresponding CoA esters [6, 9]. This dual substrate capacity ensures that the conversion of L-phenylalanine to cinnamic acid by RsTAL does not lead to wasted resources but instead results in the productive synthesis of the flavanone piconembrin. We opted to use A. thaliana as the source for the third enzyme, CHS, not only because it had been utilized in previous studies [17] but also because a cDNA library was readily available, thus circumventing the need for both plant cultivations and RNA preparations. Although we also intended to acquire CHI from this library, difficulties during gene amplification ultimately led us to pursue the direct synthesis of the desired locus using oligonucleotide gene assembly [11]. The sequence of CHI from P. lobata was chosen for this purpose due to its demonstrated performance in prior investigations [9] and was additionally codon-optimized to ensure adequate expression in E. coli.

Construction and Evaluation of pCS204 Performance

Rather than assembling the genes RsTAL, Sc4CL, AtCHS, and PlCHI$^{sym}$ into a single polycistronic operon, we decided to equip each locus with its own trc promoter to facilitate strong expression within E. coli. This four-gene biosynthetic cluster was constructed by sequential cloning into the pTrcHis2B vector to yield the plasmid pCS204. In our initial tests of this plasmid, we chose to monitor the production and accumulation of p-coumaric acid and naringenin to determine the functionality of this pathway within E. coli. Two distinct strain backgrounds and media formulations were examined during these experiments—a wild-type E. coli K12 with 500 mg/l of L-tyrosine supplementation and a previously engineered strain P2 [10] with the capacity for high endogenous L-tyrosine production (~400 mg/l L-tyrosine). Although the results obtained for the latter strain are the most relevant to our target application, we conducted parallel experiments with E. coli K12 in order to identify potential discrepancies between the consumption of endogenously-produced and externally supplemented aromatic precursors. Cultivations were conducted in 50 ml MOPS minimal medium at 30° C. with IPTG promoter induction performed during culture inoculation.

Contrary to our expectations, strains that were grown for more than 48 hr yielded only small amounts of p-coumaric acid (less than 1 mg/l) and non-detectable levels of naringenin. Because other recent studies have relied on supplementation at the level of p-coumaric acid [7, 8, 18], we suspected that TAL activity may exist as a major bottleneck in these strains. We therefore decided to repeat the experiment with p-coumaric acid in the medium in order to bypass the TAL step and test the performance of the last three genes of the pathway. Unfortunately, no measurable levels of naringenin were recovered even for this case, a result which strongly suggests the presence of severe functional deficiencies within both TAL and at least one other enzyme of this heterologous pathway.

An Abundance of Rare Codons May Limit Heterologous Protein Expression

Our initial hypothesis was that expression of these proteins may simply be poor in E. coli, leading to the apparent lack of functionality of these enzymes. Of the possible reasons for this weak expression, codon biases among different organisms are often implicated, particularly during the construction of heterologous pathways [19]. Indeed, a quick examination of the codon usage of the flavonoid biosynthetic cluster lent incredible support to this theory. As seen in Table 4, RsTAL, Sc4CL, and AtCHS require the use of several rare codons in *E. coli*. In particular, the greatest offenders seem to be the amino acid/codon pairs of proline/CCC, glycine/GGA, and arginine/CGG, with some proteins requiring up to 21 instances of the same charged tRNA species for the synthesis of a single polypeptide.

It is clear from this analysis that the presence of rare codons could present a genuine challenge in the translation of these flavonoid enzymes. To address this possibility, we decided to transform the engineered strains with pRARE2, a commercially-available plasmid which enables the IPTG-inducible overexpression of many of these rare codon tRNAs. If problems with flavonoid production are indeed related to the poor translational capacities of our strains, then supplying this plasmid should result in gains in both protein expression and enzyme activity. Unfortunately, pRARE2 had no discernible effects on p-coumaric acid or naringenin levels, which remained low or undetectable regardless of strain background (*E. coli* K12 or P2) or precursor supplementation (L-tyrosine and p-coumaric acid). Thus, it seems that this inability to produce flavonoids may not be a mere result of poor protein expression but may instead be related to inherent deficiencies in enzyme activity.

Despite our best efforts, the construction of a four-gene flavonoid biosynthetic cluster was unsuccessful in eliciting naringenin synthesis from strains that were cultivated in or produced a high endogenous level of the precursor, L-tyrosine. In addition, because our analytical methods were limited to the detection of only L-tyrosine, cinnamic acid, p-coumaric acid, and naringenin, results from these early experiments offered no direct clues regarding the core problems of the system. These first failed attempts have clearly established a need to adopt a more systematic route for engineering flavonoid production within these strains. In the next sections, we describe such an approach for the step-wise validation and optimization of each successive enzyme of the pathway.

Comparison of TAL Sources

Because very little p-coumaric acid (less than 1 mg/l) was seen with pCS204, our first goal was to demonstrate that high levels of p-coumaric acid production can in fact be recovered from our engineered strains. To demonstrate the feasibility of this process, we decided to analyze the performance of TAL in both *E. coli* K12 and P2 in the absence of the other downstream flavonoid enzymes 4CL, CHS, and CHI. Since such strains do not possess any endogenous pathways for p-coumaric acid consumption, the levels of p-coumaric acid in the culture supernatant should accurately reflect the conversion potential of the TAL enzyme being evaluated.

Figure 2:
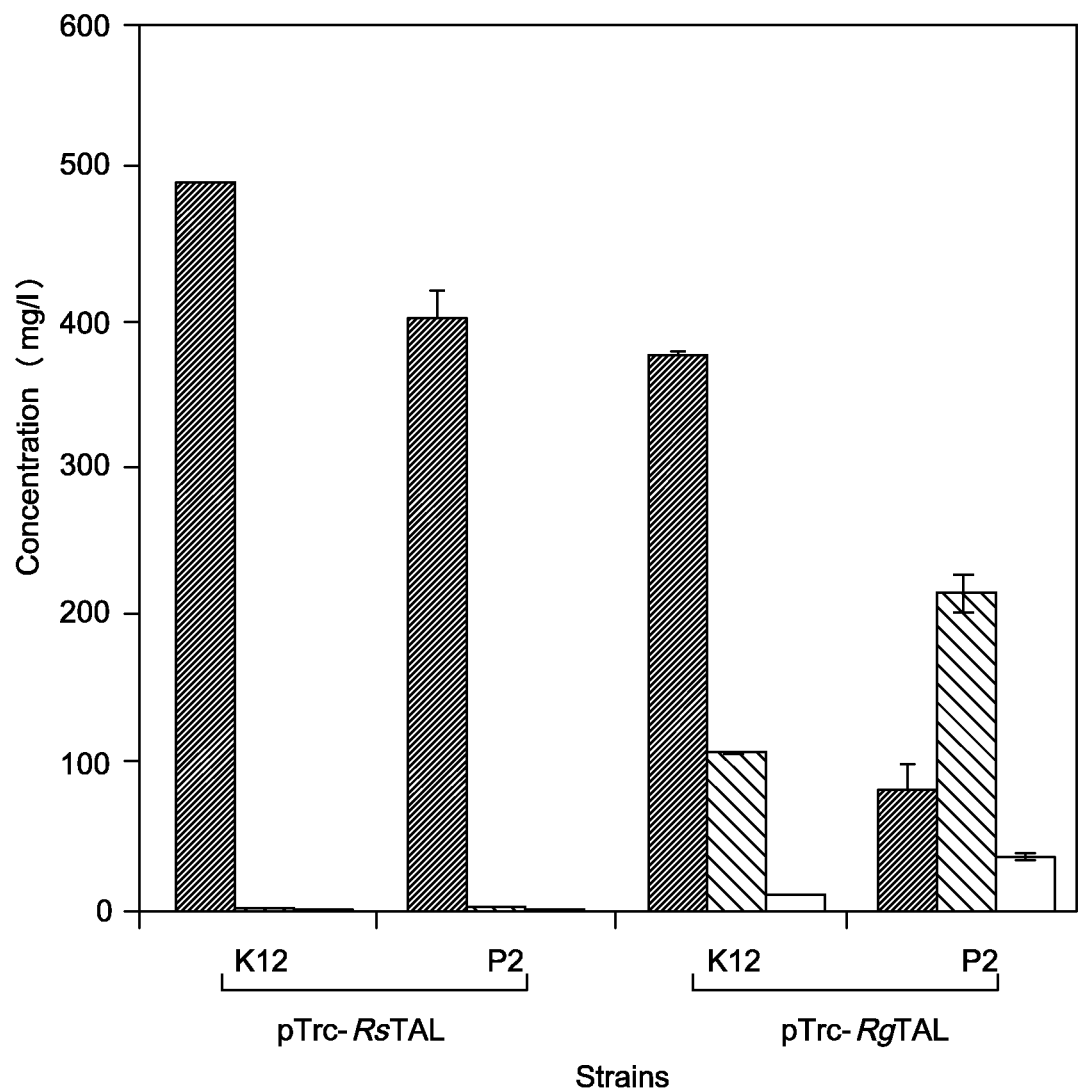
FIG. 2 shows a comparison of tyrosine ammonia lyase (TAL) activity. Concentration of L-tyrosine (black), p-coumaric acid (gray), and cinnamic acid (white) in strains containing plasmid-expressed *R. sphaeroides* TAL (pTrc-RsTAL) or *R. glutinis* TAL (pTrc-RgTAL). K12 strain cultures were supplemented with 500 mg/l L-tyrosine. Values are reported after 72 hr cultivation in MOPS minimal medium.

When RsTAL activity was tested under these experimental conditions, the same problems previously observed with the full biosynthetic gene cluster quickly emerged. As seen in FIG. 2, p-coumaric acid levels were prohibitively low, with values ranging between just 1.5 and 5.5 mg/l. Thus, our initial suspicions were confirmed: the activity of this particular TAL variant was simply not adequate for our intended application. Although we did not provide the rare codon plasmid pRARE2 to assist with translation during these studies, we inferred from previous data that similar results would have likely been obtained.

The mediocre performance of RsTAL required us to refocus our efforts on the identification of new TAL variants with the requisite expression and catalytic profiles. In particular, our search through the literature led us to explore TAL from the red yeast *R. glutinis* (RgTAL), which exhibited the strongest preference for L-tyrosine over L-phenylalanine and the highest specific activity when evaluated against seven other bacterial and fungal TAL enzymes [20]. Moreover, a direct comparison of purified RsTAL and RgTAL revealed that the catalytic activity ($K_{cat}/K_M$) of the latter on L-tyrosine was more than twelve-fold better than what was observed with RsTAL [21]. Although separate investigations on both variants reported a range of values for these specific kinetic parameters [16, 20-22], it is clear by at least a first approximation that RgTAL may be a suitable alternative for our application. To immediately bypass any potential issues with protein expression, we decided to have the RgTAL sequence codon optimized for *E. coli* and synthesized for direct cloning into pTrcHis2B.

Under the same experimental conditions as before, we observed that strains overexpressing RgTAL$^{syn}$ acquired a substantial capacity for p-coumaric acid synthesis. As seen in FIG. 2 and Table 5, *E. coli* K12 with RgTAL$^{syn}$ produced more than 104 mg/l p-coumaric acid from 500 mg/l of supplemented L-tyrosine. Similarly, P2 with RgTAL$^{syn}$ was successful in generating 213 mg/l p-coumaric acid, a titer that is actually quite competitive with the amounts typically added to the medium for flavonoid production (3 mM, 493 mg/l p-coumaric acid) [7, 8]. Since RgTAL does exhibit activity on both L-tyrosine and L-phenylalanine, low levels of cinnamic acid (9-25 mg/l) were also recovered from the culture supernatant.

Addition of Sc4CL Abolishes RgTAL$^{syn}$ Activity

Having finally verified the functionality and performance of the TAL-catalyzed step, we decided to continue our work by reintroducing the 4CL enzyme into these RgTAL$^{syn}$-expressing strains. Surprisingly, however, adding Sc4CL onto pTrc-RgTAL$^{syn}$ completely abolished p-coumaric acid accumulation, with measured titers falling to 7 mg/l in *E. coli* K12 and just 0.7 mg/l in P2 (Table 5). Although our initial hope was that this drop was related to p-coumaric acid consumption by 4CL to form coumaroyl-CoA, this notion was immediately refuted by the high concentrations of L-tyrosine still present in the media. Thus, it seemed that the addition of Sc4CL imposed some unknown impediment on TAL activity, leading once again to a nonfunctional biosynthetic cluster.

Although previous studies have shown that RgTAL can be inhibited by fairly low levels of p-coumaric acid [23], to our knowledge, there have been no reports of either 4CL or its biochemical product exerting any regulation on TAL. As a result, we initially hypothesized that these observed effects may simply be related to peculiarities in transcribing or translating these two genes from the same plasmid. To test this theory, we decided to provide Sc4CL on a separate vector (pACYC-Sc4CL) to ascertain whether this simple change could recover p-coumaric acid production in these strains. Unfortunately, for *E. coli* K12, measured p-coumaric acid levels were comparable to those seen with a single plasmid, indicating that improper tandem gene expression was not the major problem within this system (Table 5). Similarly, only small gains were seen in P2, with final p-coumaric acid titers reaching only 9% of the value seen with TAL expression alone.

Testing Other 4CL Enzyme Sources

Since the observed effects clearly did not arise from the tandem arrangement of RgTAL$^{syn}$ and Sc4CL, we decided to explore whether this phenomenon was common among all 4CL variants. Similar experiments were conducted using a new 4CL enzyme from *P. crispus* (parsley), which was selected based on its proven efficacy for other similar applications [7, 8]. As with RgTAL, the genetic sequence of Pc4CL was codon optimized for expression in *E. coli* and synthesized prior to cloning. Once again, however, no increases in p-coumaric acid production were observed for either strain background tested (*E. coli* K12 and P2) (Table 5), suggesting that this response may be a generic property common to most, if not all, 4CL enzymes.

Balancing Relative Gene Expression to Optimize Flux

Given such inconclusive results, we chose to revisit the possibility that 4CL-mediated regulatory mechanisms may be negatively impacting TAL activity. Although we found no previous reports on TAL-4CL interactions in the literature, we postulated that the buildup of the 4CL biochemical product, coumaroyl-CoA, may exert a feedback inhibitory effect on the TAL enzyme. We therefore decided to reintroduce the downstream enzymes CHS and CHI, an addition which we hoped would prevent the accumulation of this intermediate and consequently, reverse any TAL inhibition within these strains.

Rather than cloning all four genes onto the same plasmid as we did with pCS204, AtCHS and PlCHI$^{sym}$ were provided on a separate vector to minimize potential pitfalls associated with the use of large plasmids (i.e. poor transformability, recombination-mediated modifications). Such an arrangement also facilitated a parallel exploration on the effects of varying promoter strengths on flavonoid production. Because all previous flavonoid studies seem to have favored the T7 promoter system over trc [7-9], we suspected that stronger expression of the biosynthetic pathway may be needed to achieve high titers.

Interestingly, as seen in Table 6, expressing all four genes under a single strength promoter (either all trc or all T7) had no significant effect on p-coumaric acid levels, which ranged between 10-19 mg/l. Although L-tyrosine concentrations were observed to be somewhat lower for the T7 system, the absence of any significant naringenin accumulation (0.09 mg/l) suggests that this discrepancy may be related to enhanced protein synthesis rather than p-coumaric acid production and consumption. Given the stringent cellular demands of expression from four T7 promoters, it would not be wholly unexpected to find lower basal levels of L-tyrosine from this overburdened cell.

Because the addition of AtCHS and PlCHI$^{sym}$ was unable to restore RgTAL$^{sym}$ activity, we remained convinced that coumaroyl-CoA accumulation may still be a lingering issue within these strains. In particular, we hypothesized that protein translation of AtCHS may be severely hindered due to the presence of several rare codons within its sequence (Table 4). With all other parameters being equal between Pc4CL$^{sym}$ and AtCHS (promoter strength, plasmid copy number), even slight deficiencies in AtCHS protein synthesis could potentially tip the scale in favor of coumaryl:CoA accumulation. To correct for such a scenario, we decided to overexpress both AtCHS and PlCHI$^{sym}$ relative to RgTAL$^{sym}$ and Pc4CL$^{sym}$. We hoped that the expression of RgTAL$^{sym}$-Pc4CL$^{sym}$ from a trc promoter and AtCHS-PlCHI$^{sym}$ from the much stronger T7 promoter could negate these translational shortcomings.

Although this newly constructed strain behaved exactly like its preceding counterparts when induced at inoculation, we observed an unexpected shift in performance upon delayed IPTG induction. In fact, the addition of IPTG at an OD$_{600}$ of 1.0 led to a complete recovery of p-coumaric acid titers, which reached levels that were comparable to that seen with RgTAL$^{sym}$ expression alone (198 mg/l) (Table 6). Although the exact regulatory mechanisms behind this 4CL-mediated phenomenon still remain a mystery, it is clear from these results that proper pathway balancing is needed to restore RgTAL activity within these strains. For reference, we note that delayed induction could not elicit similar gains in other "unbalanced" strains (data not shown).

Despite these promising results, naringenin levels unfortunately remained quite low in this improved strain (0.61 mg/l). We hypothesized that inherent deficiencies in either AtCHS or PlCHI$^{sym}$ may now exist as the next bottlenecks for flavonoid production and therefore shifted our attention towards optimizing these final two enzymatic steps of the pathway.

Testing Alternate Sources for CHS and CHI

Due to technical limitations with the detection of both coumaroyl-CoA and the naringenin chalcone, it was difficult for us to quickly ascertain which of the two enzymes—AtCHS or PlCHI$^{sym}$—presented the next rate-limiting step of the pathway. Rather than attempting to extensively characterize each enzyme, we opted to simply swap out both genes in favor of two variants which have previously shown enormous potential in related applications [7, 8, 18]. Specifically, CHS from *P. hybrida* and CHI from *M. sativa* were tested for their ability to impart a naringenin production phenotype upon these strains. As before, we also decided to explore the use of different strength promoters to ascertain which cluster configurations could yield the best performers.

As seen in Table 7, expressing all four flavonoid genes (RgTAL$^{sym}$, Pc4CL$^{sym}$, PhCHS, MsCHI) under T7 promoters led to a 10-fold increase in naringenin production (0.6 mg/l up to 6 mg/l), even in the absence of a balanced pathway. Thus, as we saw with RsTAL and RgTAL, these results clearly highlight the importance of selecting an appropriate enzyme source/variant during the construction of these types of heterologous pathways. Additional gains were found by transferring PhCHS and MsCHI onto a constitutive promoter ($P_{GAP}$) to drive protein expression from the beginning of the culture, with naringenin titers reaching 9 mg/l. However, as we expected from our previous analysis, the most significant increases were only observed after combining a constitutively-expressed PhCHS and MsCHI gene cluster with trc-driven RgTAL$^{sym}$ and Pc4CL$^{sym}$. As evidence of a properly balanced pathway, p-coumaric acid levels increased to 136 mg/l from just 39 mg/l in the previous strain, indicating complete recovery of RgTAL$^{sym}$ activity. More notably, however, this augmented precursor pool had a direct impact on naringenin production, which increased once again by a remarkable three-fold to yield a final titer of 29 mg/l.

To put these results into perspective, we note that the best performing base strain reported in the literature (E2 containing Pc4CL-2, PhCHS, and MsCHI) had the capacity to produce 42 mg/l naringenin from 3 mM (493 mg/l) of supplemented p-coumaric acid [7]. Although our final titers still fall a bit short of this value, this strain is capable of synthesizing naringenin directly from glucose, thus eliminating all reliance on expensive phenylpropanoic acid precursors. Given the several hundred-fold difference in the price of these two substrates (glucose versus p-coumaric acid), it is clear that the sheer economics of the process make this a superior alternative to all other strains developed thus far. In addition, studies with E2 report a maximum OD$_{600}$ of just 2 in minimal medium, thus hinting at potential problems with cell viability in these cultures [7]. In stark contrast, our constructed strain consistently grew to an OD$_{600}$ of 4.5, signifying a fairly robust constitution that would be amenable to future engineering efforts.

Engineering Malonyl-CoA Availability

As demonstrated in numerous reports, the supply of malonyl-CoA often appears as the next major bottleneck of the phenylpropanoid pathway due to both the requirement for three malonyl-CoA molecules and the low basal levels of this metabolite found within the cell [24]. As a result, several recent publications have focused on developing novel strategies for increasing the pool of this important precursor molecule [7-9, 18]. Rather than repeating all these efforts in this study, we instead focused on the application of two specific techniques for increasing malonyl-CoA supplies and hopefully, in turn, improving naringenin production. The first strategy utilizes a recombinant malonate assimilation pathway from *Rhizobium trifolii* (MatB and MatC) for both the transport of supplemented malonate into the cell, as well as its subsequent conversion to malonyl-CoA. The second makes use of the fatty acid pathway inhibitor cerulenin, which represses both fabB and fabF, thus limiting the amount of malonyl-CoA lost to the synthesis of fatty acids [8].

As seen in Table 8, the addition of both malonate (2 g/l) and *R. trifolii* MatB and MatC (RtMATBC) resulted in a 59% increase in naringenin over the previously constructed strain, with titers reaching 46 mg/l after 48 hr. However, the most significant gains were obtained with cerulenin supplementation, which led to an increase of over 190% and a final titer of 84 mg/l naringenin. Although the high cost of cerulenin prohibits its widespread use in industrial fermentation processes, these results clearly demonstrate that additional gains in flavonoid production can be engineered by manipulating malonyl-CoA production and utilization within this strain. Thus, we remain confident that other established malonyl-CoA engineering strategies can be successfully implemented for the construction of a superior flavonoid producer.

Naringenin Production in rpoA14$^R$

Although P2 was used as the background strain for all our experiments, we recently reported the construction of several other L-tyrosine producers which possessed more than twice the yields and titers observed with P2 [10]. Given such significant improvements in performance, we were naturally curious to see if these phenotypically superior strains could surpass P2 in the production of flavonoid compounds as well. We decided to explore this potential using the completely genetically-defined strain, rpoA14$^R$, which was reported to produce more than 900 mg/l L-tyrosine in 50 ml cultures. As seen in Table 8, final naringenin titers in rpoA14$^R$ in both the presence and absence of cerulenin were actually quite comparable to those seen with P2, indicating that malonyl-CoA rather than L-tyrosine truly is the limiting precursor of the pathway. However, it was interesting to note that in contrast to P2, rpoA14$^R$ exhibited an unusually enhanced capacity for p-coumaric acid synthesis, generating 315-364 mg/l p-coumaric acid after 48 hr. Because these p-coumaric acid concentrations approach those typically used in supplementation experiments, it is clear that future endeavors for engineering microbial flavonoid production could surely benefit from the use of this superior base strain.

Conclusions

Lessons Learned in Heterologous Pathway Construction

In these studies, we have successfully demonstrated the feasibility of utilizing a set of engineered L-tyrosine producers for the synthesis of flavonoid compounds from glucose. Successes in this avenue did not come easily, however, as we experienced several nuances in the construction and assembly of heterologous pathways. During this investigation, we discovered the incredible sensitivity of this pathway to specific enzyme variants, with certain genetic sources (RgTAL, Pc4CL, PhCHS, MsCHI) exhibiting much higher in vivo activities than others (RsTAL, Sc4CL, AtCHS, PlCHI). Because these observed discrepancies likely result from an aggregate of factors including protein expression, proper folding, and the enzyme's innate catalytic properties, it becomes quite difficult to make a priori predictions on the relative performance of such variants. We were therefore quite fortunate to have some of this information available to us from prior studies and comparisons conducted by other laboratories.

During the course of these experiments, we also encountered a previously uncharacterized regulatory phenomenon involving 4CL-mediated suppression of TAL enzyme activity. We hypothesized that these effects may be due to the accumulation of and subsequent feedback inhibition by coumaroyl-CoA, a theory that was corroborated by the recovery of TAL activity through adequate pathway balancing. This requirement for gene expression optimization is not an unusual feature of heterologous pathways, particularly for those that may result in the production of potentially toxic intermediates within the cell. As such, several semi-combinatorial tools or approaches have been constructed for the specific purpose of finding these relative expression optima [25-27]. Although experimenting with these parameters may result in improved production of the precursor p-coumaric acid, our most recent results suggest that engineering malonyl-CoA production, at least for the short-term, may have a more significant impact on final naringenin titers.

Demonstrated Feasibility of Microbial Flavonoid Production from Glucose

Although other laboratories have demonstrated the value and potential of developing microbial-based processes for flavonoid production, these previous methodologies suffered from two significant shortcomings—the requirement for expensive phenylpropanoic precursors and the need for two separate stages of cultivation for biomass/protein generation and flavonoid production. In this study, we discussed the development of a set of strains and protocols possessing the capacity to circumvent both of these problems. The use of previously-engineered L-tyrosine producers [10] enabled us to address the first issue, with the assembly and optimization of a heterologous flavonoid pathway leading to the unique ability to produce naringenin directly from glucose. To our knowledge, this is the first substantiated example of flavonoid synthesis without the presence of expensive phenylpropanoic precursors in the media. Because recovered titers by these engineered strains were comparable to those previously achieved with the addition of p-coumaric acid, such an accomplishment roughly translates into a several hundred fold decrease in substrate-related expenses. This drastic reduction in cost clearly provides great economic impetus for continuing these metabolic engineering pursuits.

Previously developed protocols for flavonoid production also required a separate step in rich media to build up biomass and biosynthetic proteins prior to cultivation in minimal media for flavonoid production. Although the rationale for this methodology has not been directly addressed by any researchers, we presume that this practice is needed to offset the poor growth and protein expression seen in minimal media. Unfortunately, the use of rich media in industrial scale processes is not only expensive but also produces less consistent and standardized results due to the undefined nature of its components. In addition, while the separation, recovery, and resuspension of biomass may appear relatively straightforward in a laboratory setting, these additional steps often result in higher equipment and operating costs when translated into an industrial-scale process. For these reasons, we were quite pleased to see that, unlike previous constructions, our engineered strains possessed robust cellular constitutions and exhibited no apparent growth deficiencies in minimal media. As such, the use of these healthy strains allowed us to develop a simplified one-medium protocol for the production of flavonoids from glucose.

To minimize fermentation times and maximize productivity, we elected to divide our fermentations into two distinct phases, the first carried out at 37° C. to maximize growth and L-tyrosine production and the second performed at 30° C. to provide an optimum temperature for heterologous enzyme expression and activity. However, since reactor conditions, such as temperature and pH, are easily controlled and manipulated, these simple parameter changes do not present any additional barriers to the scale-up and implementation of this process. As a final comment, we note that the simplification of this protocol did not require us to make sacrifices in either yield or productivity, as strain performance was found to be quite comparable to studies utilizing the previously established two-step procedure.

Further Improvements by Engineering Malonyl-CoA Availability

The results from our cerulenin supplementation experiments clearly indicate a need to engineer malonyl-CoA availability to further improve naringenin yields and titers in these strains. Fortunately, several investigations have already highlighted potential avenues for introducing such cellular changes through a combination of both rational and model-guided approaches. In one particularly relevant study, researchers found that the simultaneous deletion of genes sdhA, adhE, brnQ, and citE and overexpression of the enzymes acetyl-CoA synthase, acetyl-CoA carboxylase, biotin ligase, and pantothenate kinase could increase naringenin levels from 42 mg/l in the base/parental strain to an impressive 270 mg/l in the engineered construct [18]. Given these past successes, we are therefore quite confident that similar gains can be made in our strains, particularly within the rpoA14$^R$ background, which already possesses a high capacity for p-coumaric acid synthesis. Indeed, such improvements would certainly bring us one step closer to developing an economically viable and scalable process for the microbial production of flavonoid compounds.

TABLE 1

| Cost of naringenin and substrates/precursors | |
| --- | --- |
| Compound | Price ($/g) |
| Naringenin | 6.46 |
| p-Coumaric acid | 2.74 |
| L-Tyrosine | 0.48 |
| Glucose | 0.01 |

*Calculated from prices of the largest available quantities on Sigma-Aldrich

TABLE 2

Primers used in this study

| Primer Name | Primer Sequence (5'→3') |
| --- | --- |
| CS313 *R. sphaeroides* hutH sense KpnI | GCTCGGTACC ATGCTCGCCATGAGCCCCC (SEQ ID NO: 1) |
| CS314 *R. sphaeroides* hutH anti HindIII | ACG AAG CTT TTA GAC GGG AGA TTG CTG CAA GAG G (SEQ ID NO: 2) |
| CS315 *S. coelicolor* 4CL-2 sense NcoI | TAA ACC ATG GTC CGC AGC GAG TAC GCA G (SEQ ID NO: 3) |
| CS316 *S. coelicolor* 4CL-2 anti HindIII | ACG AAG CTT TTA TCG CGG CTC CCT GAG CTG T (SEQ ID NO: 4) |
| CS317 *A. thaliana* CHS sense NcoI | TAA ACC ATG GTG ATG GCT GGT GCT TCT TCT T (SEQ ID NO: 5) |
| CS318 *A. thaliana* CHS anti KpnI | GCT CGG TAC CTT AGA GAG GAA CGC TGT GCA AGA CG (SEQ ID NO: 6) |
| CS420 CHI sense KpnI | GCT CGG TAC CAT GGC TGC GGC TGC TGC C (SEQ ID NO: 7) |
| CS421 CHI anti HindIII | ACG AAG CTT TTA CAC AAT AAT ACC GTG GCT CAA CAC G (SEQ ID NO: 8) |
| CS481 pTrc 4CL sense[a] | ACG AAG CTT AAT CCT AGG AAC TGA AAT GAG CTG TTG ACA ATT AAT CAT CC (SEQ ID NO: 9) |
| CS482 pTrc 4CL anti[b] | ACG AAG CTT CTT GGA TCC CGA TCC GGA AAT TAT CGC GGC TCC CTG AGC TGT (SEQ ID NO: 10) |
| CS483 pTrc CHI sense[c] | GAG TTC GAA CGA TGT ACA AAC TGA AAT GAG CTG TTG ACA ATT AAT CAT CC (SEQ ID NO: 11) |
| CS484 pTrc CHI anti 1[d] | GCT AGC TTC GTA CGT GCT GAG CAT ATC AAT TGA TTA CAC AAT AAT ACC GTG GCT CAA CAC G (SEQ ID NO: 12) |
| CS485 pTrc CHI anti 2[d, e] | GAG TTC GAA CTC GAG ATA CTA GTG TAG ATC TTT GGC CTC GCT GGC CAT GCT AGC TTC GTA CGT GCT GAG CAT ATC (SEQ ID NO: 13) |
| CS486 CHS-CHI sense BamHI | CTT GGA TCC GCC GAC ATC ATA ACG GTT CTG GC (SEQ ID NO: 14) |

TABLE 2-continued

Primers used in this study

| Primer Name | Primer Sequence (5'→3') |
|---|---|
| CS487 CHS-CHI anti BamHI | CTT GGA TCC GAG TTC GAA CTC GAG ATA CTA GTG TAG ATC TTT GGC (SEQ ID NO: 15) |
| CS619 tal sense NcoI | TAA ACC ATG GCG CCT CGC C (SEQ ID NO: 16) |
| CS620 tal anti SalI | AAT GTC GAC TTA TGC AGC CAT CTT CAG CAG AAC ATT (SEQ ID NO: 17) |
| CS621 4CL sense NdeI | GCA CTA ACA TAT GGG TGA CTG CGT TGC CCC (SEQ ID NO: 18) |
| CS622 4CL anti AvrII | AAT CCT AGG TTA CTT CGG CAG GTC GCC (SEQ ID NO: 19) |
| CS627 CHS sense NdeI | TAA CAT ATG GTG ATG GCT GGT GC (SEQ ID NO: 20) |
| CS628 CHS anti AvrII | AAT CCT AGG TTA GAG AGG AAC GCT GTG CAA GAC G (SEQ ID NO: 21) |
| CS629 CHI sense NcoI | TAT ACC ATG GCT GCG GCT GCT G (SEQ ID NO: 22) |
| CS630 CHI anti NotI | TAA GCG GCC GCT TAC ACA ATA ATA CCG TGG CTC AAC ACG (SEQ ID NO: 23) |
| CS644 lacI sense AatII | CAT GAC GTC CCG CTT ACA GAC AAG CTG TGA CCG (SEQ ID NO: 24) |
| CS645 CHI anti BsiWI | GCT TCG TAC GTG CTG AGC ATA TCA ATT (SEQ ID NO: 25) |
| CS786 tal sense FseI | TAA CGG CCG GCC CCG ACA TCA TAA CGG TTC TGG CA (SEQ ID NO: 26) |
| CS787 rrnB anti BamHI | TAA GGA TCC AAC AGA TAA AAC GAA AGC CCA GTC T (SEQ ID NO: 27) |
| CS792 BsrGI-BglII oligo 1 | GTA CGC GCA TGC GC (SEQ ID NO: 28) |
| CS793 BsrGI-BglII oligo 2 | GAT CGC GCA TGC GC (SEQ ID NO: 29) |

[a]Underlined segments indicate the addition of AvrII and HindIII restriction sites
[b]Underlined segments indicate the addition of BspEI, BamHI, and HindIII restriction sites
[c]Underlined segments indicate the addition of BsrGI and BstBI restriction sites
[d]Underlined segments indicate the addition of a multicloning site (MfeI, BlpI, BsiWI, NheI, SfiI, SpeI, XhoI)
[e]Bold segment indicates addition of a BstBI restriction site

TABLE 3

Plasmids and strains used in this study

| Plasmid or Strain | Relevant characteristics | Source |
|---|---|---|
| Plasmids | | |
| pTrcHis2B | trc promoter, pBR322 ori, Amp[R] | Invitrogen |
| pTrcsGFP | pTrcHis2B carrying a superfolder GFP (sGFP) variant [13] that was synthesized and codon-optimized for E. coli | C. Santos, unpublished |
| pACYC184 | p15A ori, Cm[R] | ATCC |
| pETDuet-1 | double T7 promoters, ColE1(pBR322) ori, Amp[R] | Novagen |
| pCDFDuet-1 | double T7 promoters, CloDF13 ori, Sp[R] | |
| pRARE2 | p15A ori, Cm[R], supplies tRNAs for the rare codons AUA, AGG, AGA, CUA, CCC, GGA, and CGG | Novagen |
| pCS204 | pTrcHis2B carrying R. sphaeroides TAL, S. coelicolor 4CL, A. thaliana CHS, and P. lobata CHI[syn] | This study |
| pTrc-RsTAL | pTrcHis2B carrying R. sphaeroides TAL | This study |
| pTrc-RgTAL[syn] | pTrcHis2B carrying codon-optimized R. glutinis TAL | This study |
| pTrc-RgTAL[syn]-Sc4CL | pTrcHis2B carrying codon-optimized R. glutinis TAL and S. coelicolor 4CL | This study |

TABLE 3-continued

Plasmids and strains used in this study

| Plasmid or Strain | Relevant characteristics | Source |
|---|---|---|
| pTrc-RgTAL$^{syn}$-Pc4CL$^{syn}$ | pTrcHis2B carrying codon-optimized *R. glutinis* TAL and codon-optimized *P. crispus* 4CL-1 | This study |
| pACYC-Sc4CL | pACYC184 carrying *S. coelicolor* 4CL | This study |
| pET-RgTAL$^{syn}$-Pc4CL$^{syn}$ | pETDuet-1 carrying codon-optimized *R. glutinis* TAL and codon-optimized *P. crispus* 4CL-1 | This study |
| pCDF-RgTAL$^{syn}$-Pc4CL$^{syn}$ | pCDFDuet-1 carrying codon-optimized *R. glutinis* TAL and codon-optimized *P. crispus* 4CL-1 | This study |
| pCDF-trc-RgTAL$^{syn}$-Pc4CL$^{syn}$ | pCDFDuet-1 carrying codon-optimized *R. glutinis* TAL and codon-optimized *P. crispus* 4CL-1 with trc promoters | This study |
| pACKm-AtCHS-PlCHI$^{syn}$ | pACKm carrying *A. thaliana* CHS and codon-optimized *P. lobata* CHI | This study |
| pCDF-AtCHS-PlCHI$^{syn}$ | pCDFDuet-1 carrying *A. thaliana* CHS and codon-optimized *P. lobata* CHI | This study |
| pET-PhCHS-MsCHI | pETDuet-1 carrying *P. hybrida* CHS and *M. sativa* CHI | [7] |
| pOM-PhCHS-MsCHI | pOM carrying *P. hybrida* CHS and *M. sativa* CHI with a single GAP (constitutive) promoter | This study |
| pACYC-MatBC | pACYCDuet-1 carrying *R. trifolii* MatB and MatC | [8] |
| Strains | | |
| *E. coli* K12 (MG1655) | wild-type | ATCC |
| P2 | *E. coli* K12 ΔpheA ΔtyrR lacZ::P$_{LtetO-1}$-tyrA$^{fbr}$ aroG$^{fbr}$ tyrR::P$_{LtetO-1}$-tyrA$^{fbr}$ aroG$^{fbr}$ | [10] |
| rpoA14$^R$ | P2 hisH(L82R) pHACM-rpoA14 | [10] |
| *E. coli* K12 (DE3) | *E. coli* K12 carrying the gene for T7 RNA polymerase | This study |
| P2 (DE3) | P2 carrying the gene for T7 RNA polymerase | This study |
| rpoA14$^R$ (DE3) | rpoA14$^R$ carrying the gene for T7 RNA polymerase | This study |

TABLE 4

Rare codons found within RsTAL, Sc4CL, AtCHS, and PlCHI$^{syn}$ sequences

| Rare codon* | RsTAL | Sc4CL | AtCHS | PlCHI$^{syn}$ |
|---|---|---|---|---|
| Pro (CCC) | 12 (43%) | 21 (50%) | 4 (21%) | 4 (40%) |
| Leu (CUA) | 1 (1%) | 0 (0%) | 6 (15%) | 0 (0%) |
| Arg (AGG) | 3 (7%) | 3 (9%) | 4 (22%) | 0 (0%) |
| Gly (GGA) | 8 (16%) | 2 (5%) | 9 (26%) | 1 (5%) |
| Arg (AGA) | 1 (2%) | 0 (0%) | 3 (17%) | 0 (0%) |
| Ile (AUA) | 0 (0%) | 0 (0%) | 5 (24%) | 1 (7%) |
| Arg (CGG) | 16 (35%) | 7 (21%) | 1 (6%) | 3 (43%) |
| TOTAL NUMBER | 41 | 33 | 32 | 9 |

*The first value denotes the number of instances that a specified codon appears within a gene/protein. The second number represents the percentage of amino acids encoded by that rare codon. Numbers appearing in bold highlight rare codons with a particularly high abundance within these gene/protein sequences.

TABLE 5

Effects of TAL/4CL expression on precursor and intermediate concentrations

| | Concentrations after 72 hr (mg/l) | | |
|---|---|---|---|
| Strain | L-Tyrosine | p-Coumaric acid | Cinnamic acid |
| *E. coli* K12 | | | |
| pTrc-RgTAL$^{syn}$ | 374 | 104 | 9 |
| pTrc-RgTAL$^{syn}$-Sc4CL | 485 | 7 | 0.3 |
| pTrc-RgTAL$^{syn}$, pACYC-Sc4CL | 569 | 9 | 3 |
| pTrc-RgTAL$^{syn}$-Pc4CL$^{syn}$ | 461 | 42 | 1 |
| P2 | | | |
| pTrc-RgTAL$^{syn}$ | 79 | 213 | 35 |
| pTrc-RgTAL$^{syn}$-Sc4CL | 503 | 0.7 | 0.6 |
| pTrc-RgTAL$^{syn}$, pACYC-Sc4CL | 484 | 19 | 12 |
| pTrc-RgTAL$^{syn}$-Pc4CL$^{syn}$ | 521 | 18 | 5 |

TABLE 6

Effects of relative gene expression on precursor and intermediate concentrations

| | Concentrations after 72 hr (mg/l) | | | |
|---|---|---|---|---|
| Strain[a] | L-Tyrosine | p-Coumaric acid | Cinnamic acid | Naringenin |
| P2[b] | | | | |
| pTrc-RgTAL$^{syn}$-Pc4CL$^{syn}$, pACKm-AtCHS-PlCHI$^{syn}$ | 496 | 10 | 21 | 0.09 |

TABLE 6-continued

Effects of relative gene expression on precursor and intermediate concentrations

| | Concentrations after 72 hr (mg/l) | | | |
|---|---|---|---|---|
| Strain[a] | L-Tyrosine | p-Coumaric acid | Cinnamic acid | Naringenin |
| pET-RgTAL[syn]-Pc4CL[syn], pCDF-AtCHS-PlCHI[syn] | 311 | 19 | 5 | 0.3 |
| pTrc-RgTAL[syn]-Pc4CL[syn], pCDF-AtCHS-PlCHI[syn] | 343 | 7 | 4 | 0.04 |
| pTrc-RgTAL[syn]-Pc4CL[syn], pCDF-AtCHS-PlCHI[syn], induced at $OD_{600} = 1.0$[c] | 84 | 198 | 48 | 0.61 |

[a]Plasmids with a pTrc or pACKm backbone contain trc promoters in front of all genes; plasmids with a pET or pCDF backbone contain T7 promoters in front of all genes. Unless indicated, all cultures were induced with 1 mM IPTG at inoculation.
[b]All T7 promoter plasmids were cultivated in a P2(DE3) background for T7 RNA polymerase expression.
[c]Growth was somewhat hampered for this strain with a maximum $OD_{600}$ of just 2.4 compared to 4-5 for other strains.

TABLE 7

Evaluation of two novel gene sources - *P. hybrida* CHS and *M. sativa* CHI - for flavonoid production

| | Concentrations (mg/l) | | | |
|---|---|---|---|---|
| Strain[a] | L-Tyrosine | p-Coumaric acid | Cinnamic acid | Naringenin |
| P2[b] | | | | |
| pCDF-RgTAL[syn]-Pc4CL[syn], pET-PhCHS-MsCHI[c] | 543 | 28 | 15 | 6 |
| pCDF-RgTAL[syn]-Pc4CL[syn], pOM-PhCHS-MsCHI[d] | 251 | 39 | 16 | 9 |
| pCDF-trc-RgTAL[syn]-Pc4CL[syn], pOM-PhCHS-MsCHI[d,e] | 397 | 136 | 24 | 29 |

[a]Plasmids with a pET or pCDF backbone contain individual T7 promoters in front of all genes unless otherwise indicated. Plasmids with a pOM backbone contain a single constitutive promoter ($P_{GAP}$) to drive expression of both genes.
[b]All T7 promoter plasmids were cultivated in a P2(DE3) background for T7 RNA polymerase expression.
[c]Cultivations were performed in 50 ml MOPS minimal medium at 30° C. with 1 mM IPTG induction at $OD_{600} = 1.0$. Measurements are shown after 72 hr.
[d]Strains were grown in 25 ml MOPS minimal medium at 37° C. After 15-20 hr, 25 ml fresh medium and 1 mM IPTG was added to the culture, and flasks were transferred to 30° C. Measurements are shown after 48 hr (total cultivation time).
[e]Although pCDF-trc-RgTAL[syn]-Pc4CL[syn] was constructed with a pCDF backbone, it contains a trc promoter in front of both genes.

TABLE 8

Engineering malonyl-CoA availability in P2 and rpoA14[R]

| | Concentrations after 48 hr (mg/l) | | | |
|---|---|---|---|---|
| Strain[a] | L-Tyrosine | p-Coumaric acid | Cinnamic acid | Naringenin |
| P2 | | | | |
| pCDF-trc-RgTAL[syn]-Pc4CL[syn], pOM-PhCHS-MsCHI[b] | 397 | 136 | 24 | 29 |
| pCDF-trc-RgTAL[syn]-Pc4CL[syn], pOM-PhCHS-MsCHI[b], pACYCMatBC + malonate | 42 | 107 | 51 | 46 |
| pCDF-trc-RgTAL[syn]-Pc4CL[syn], pOM-PhCHS-MsCHI[b] + cerulenin | 439 | 79 | 25 | 84 |
| rpoA14[R] | | | | |
| pCDF-trc-RgTAL[syn]-Pc4CL[syn], pOM-PhCHS-MsCHI[b] | 187 | 364 | 107 | 29 |
| pCDF-trc-RgTAL[syn]-Pc4CL[syn], pOM-PhCHS-MsCHI[b] + cerulenin | 175 | 315 | 101 | 77 |

[a]Strains were grown in 25 ml MOPS minimal medium at 37° C. After 15-20 hr, 25 ml fresh medium and 1 mM IPTG was added to the culture, and flasks were transferred to 30° C. Measurements are shown after 48 hr (total cultivation time).

TABLE S1

DNA and protein sequences of synthesized genes and proteins

| Gene | DNA/Protein Sequence |
| --- | --- |
| *P. lobata* chalcone isomerase (PlCHI$^{syn}$) (DNA) | ATGGCTGCGGCTGCTGCCGTGGCGACCATTAGCGCGGTGCAAGTGGAG<br>TTTCTGGAATTTCCAGCGGTAGTGACCAGCCCGGCATCAGGCCGTACC<br>TATTTTCTTGGTGGCGCTGGGGAGCGTGGCCTGACGATTGAGGGCAAG<br>TTTATCAAGTTCACCGGCATTGGCGTGTATTTGGAAGATAAGGCGGTT<br>AGCTCCCTGGCGGCGAAATGGAAAGGCAAACCGAGCGAAGAACTGGT<br>GGAGACCCTGGACTTCTACCGGGATATCATAAGCGGTCCCTTCGAGAA<br>ACTGATCCGTGGCAGCAAAATTCTGCCACTGTCGGGCGTCGAATACAG<br>CAAGAAAGTGATGGAAAACTGCGTGGCGCATATGAAAAGCGTCGGAA<br>CCTATGGCGATGCGGAAGCCGCTGCCATCGAGAAGTTCGCGGAGGCCT<br>TCAAAAACGTGAATTTTCAACCTGGCGCGACCGTGTTTTATCGGCAAA<br>GCCCAGATGGCGTTCTGGGCCTGAGTTTCAGCGAGGATGTGACCATTC<br>CCGATAATGAAGCGGCGGTGATTGAAAACAAAGCCGTCTCCGCTGCGG<br>TGTTAGAAACCATGATTGGCGAACATGCAGTAAGCCCCGATCTGAAAC<br>GTAGCTTGGCGAGCCGGTTACCCGCCGTGTTGAGCCACGGTATTATTGT<br>GTAA (SEQ ID NO: 30) |
| *P. lobata* chalcone isomerase (PlCHI$^{syn}$) (Protein) | MAAAAAVATISAVQVEFLEFPAVVTSPASGRTYFLGGAGERGLTIEGKFIK<br>FTGIGVYLEDKAVSSLAAKWKGKPSEELVETLDFYRDIISGPFEKLIRGSKI<br>LPLSGVEYSKKVMENCVAHMKSVGTYGDAEAAAIEKFAEAFKNVNFQPG<br>ATVFYRQSPDGVLGLSFSEDVTIPDNEAAVIENKAVSAAVLETMIGEHAVS<br>PDLKRSLASRLPAVLSHGIIV (SEQ ID NO: 31) |
| *R. glutinis* tyrosine ammonia lyase (Rgtal$^{syn}$) (DNA) | ATGGCGCCTCGCCCGACTTCGCAAAGCCAGGCCCGCACTTGCCCGACG<br>ACGCAGGTTACCCAAGTTGATATCGTTGAGAAAATGTTGGCGGCTCCT<br>ACTGATAGCACGCTGGAGCTGGACGGTTATAGCCTGAATCTGGGTGAT<br>GTCGTGAGCGCTGCGCGTAAGGGTCGTCCTGTCCGTGTCAAAGATAGC<br>GATGAAATCCGCAGCAAAATCGACAAGAGCGTTGAATTCCTGCGCAGC<br>CAACTGAGCATGTCGGTTTACGGTGTGACGACCGGCTTTGGCGGCTCC<br>GCGGACACGCGCACGGAGGACGCAATTAGCCTGCAAAAGGCGTTGCT<br>GGAACACCAGCTGTGTGGTGTGTTGCCGAGCAGCTTCGACAGCTTTCG<br>CTTGGGTCGTGGTCTGGAGAATAGCCTGCCGTTGGAAGTCGTTCGCGG<br>TGCAATGACCATTCGTGTGAATTCGCTGACCCGTGGCCATAGCGCTGTT<br>CGTCTGGTTGTTCTGGAAGCACTGACGAACTTTCTGAACCACGGTATTA<br>CCCCGATTGTTCCGCTGCGCGGTACGATCTCCGCGAGCGGCGATCTGTC<br>TCCACTGTCGTACATTGCAGCGGCGATTAGCGGTCACCCGGATAGCAA<br>AGTTCACGTGGTCCATGAAGGCAAAGAGAAGATCCTGTACGCGCGCGA<br>AGCGATGGCGCTGTTTAACCTGGAGCCGGTGGTTTTGGGTCCGAAGGA<br>GGGCCTGGGTCTGGTGAATGGTACGGCAGTCTCCGCGAGCATGGCAAC<br>GCTGGCACTGCACGACGCGCATATGTTGAGCCTGTTGAGCCAATCGCT<br>GACCGCGATGACCGTGGAGGCGATGGTCGGTCACGCGGGCAGCTTCCA<br>TCCATTCCTGCACGATGTTACGCGTCCGCACCCGACGCAAATCGAGGT<br>CGCGGGTAACATTCGCAAACTGCTGGAGGGCTCGCGCTTCGCGGTCCA<br>CCACGAGGAAGAGGTTAAGGTCAAGGATGATGAAGGCATTTTGCGTCA<br>GGATCGTTATCCGTTGCGCACGAGCCCGCAATGGTTGGGTCCGCTGGT<br>GTCCGACCTGATTCACGCTCATGCCGTCTTGACGATCGAAGCGGGTCA<br>AAGCACCACCGATAACCCACTGATCGATGTTGAGAATAAGACCAGCCA<br>TCACGGTGGCAACTTTCAAGCGGCAGCGGTTGCCAACACGATGGAAAA<br>GACCCGTCTGGGCTTGGCCCAAATCGGTAAACTGAATTTCACCCAGCT<br>GACGGAGATGCTGAACGCGGGCATGAATCGTGGCTTGCCGAGCTGCCT<br>GGCGGCTGAAGACCCATCCCTGAGCTATCATTGCAAAGGTCTGGACAT<br>TGCGGCGGCTGCATATACGAGCGAACTGGGCCACCTGGCTAACCCGGT<br>CACCACCCACGTCCAACCGGCTGAAATGGCAAACCAGGCGGTGAATA<br>GCTTGGCGTTGATTAGCGCACGTCGTACCACGGAATCTAACGACGTTC<br>TGTCCCTGCTGCTGGCAACGCACCTGTACTGCGTGCTGCAGGCGATCG<br>ACCTGCGTGCGATTGAGTTCGAGTTCAAGAAACAGTTTGGTCCTGCCA<br>TTGTTAGCCTGATCGACCAACACTTTGGTAGCGCGATGACGGGTAGCA<br>ATCTGCGTGATGAGCTGGTTGAAAAGGTCAATAAGACTCTGGCCAAGC<br>GTTTGGAGCAAACCAATAGCTACGATCTGGTTCCGCGCTGGCACGACG<br>CTTTTAGCTTCGCTGCAGGCACTGTTGTCGAGGTTCTGTCCAGCACGAG<br>CCTGAGCTTGGCGGCCGTGAACGCATGGAAGGTTGCGGCAGCCGAGA<br>GCGCGATCTCCTTGACGCGCCAGGTCCGTGAAACGTTTTGGTCCGCTGC<br>AAGCACCTCCAGCCCGGCGTTGTCTTACTTGAGCCCGCGCACGCAGAT<br>CCTGTACGCATTTGTGCGTGAGGAACTGGGTGTCAAAGCCCGCCGTGG<br>TGACGTCTTCTTGGGTAAACAAGAAGTTACCATCGGCAGCAACGTTAG<br>CAAGATTTACGAAGCCATCAAGAGCGGCCGTATCAACAATGTTCTGCT<br>GAAGATGCTGGCATAA (SEQ ID NO: 32) |
| *R. glutinis* tyrosine ammonia lyase (Rgtal$^{syn}$) (Protein) | MAPRPTSQSQARTCPTTQVTQVDIVEKMLAAPTDSTLELDGYSLNLGDVV<br>SAARKGRPVRVKDSDEIRSKIDKSVEFLRSQLSMSVYGVTTGFGGSADTRT<br>EDAISLQKALLEHQLCGVLPSSFDSFRLGRGLENSLPLEVVRGAMTIRVNS<br>LTRGHSAVRLVVLEALTNFLNHGITPIVPLRGTISASGDLSPLSYIAAAISGH<br>PDSKVHVVHEGKEKILYAREAMALFNLEPVVLGPKEGLGLVNGTAVSAS<br>MATLALHDAHMLSLLSQSLTAMTVEAMVGHAGSFHPFLHDVTRPHPTQI<br>EVAGNIRKLLEGSRFAVHHEEEVKVKDDEGILRQDRYPLRTSPQWLGPLV<br>SDLIHAHAVLTIEAGQSTTDNPLIDVENKTSHHGGNFQAAAVANTMEKTR<br>LGLAQIGKLNFTQLTEMLNAGMNRGLPSCLAAEDPSLSYHCKGLDIAAAA |

TABLE S1-continued

DNA and protein sequences of synthesized genes and proteins

| Gene | DNA/Protein Sequence |
|---|---|
| | YTSELGHLANPVTTHVQPAEMANQAVNSLALISARRTTESNDVLSLLLAT<br>HLYCVLQAIDLRAIEFEFKKQFGPAIVSLIDQHFGSAMTGSNLRDELVEKV<br>NKTLAKRLEQTNSYDLVPRWHDAFSFAAGTVVEVLSSTSLSLAAVNAWK<br>VAAAESAISLTRQVRETFWSAASTSSPALSYLSPRTQILYAFVREELGVKA<br>RRGDVFLGKQEVTIGSNVSKIYEAIKSGRINNVLLKMLA (SEQ ID NO: 33) |
| P. crispus 4-coumarate:coA ligase (Pc4CL$^{sym}$) (DNA) | ATGGGTGACTGCGTTGCCCCGAAAGAGGATCTGATCTTCCGCAGCAAA<br>CTGCCGGACATTTACATTCCAAAGCATCTGCCGCTGCATACGTATTGTT<br>TTGAGAATATCAGCAAGGTTGGCGACAAGAGCTGTCTGATCAACGGCG<br>CAACCGGCGAAACGTTTACCTACAGCCAGGTCGAGCTGCTGTCCCGTA<br>AAGTTGCCAGCGGCCTGAACAAGCTGGGCATTCAACAAGGTGATACCA<br>TTATGCTGTTGCTGCCGAATTCCCCGGAGTACTTTTTCGCTTTCCTGGGT<br>GCGAGCTATCGCGGTGCAATCAGCACCATGGCGAATCCATTCTTTACC<br>AGCGCAGAAGTGATCAAGCAACTGAAAGCGAGCCAAGCGAAGCTGAT<br>TATCACCCAGGCATGCTATGTTGACAAGGTCAAGGACTACGCAGCGGA<br>GAAAAACATCCAGATCATTTGTATTGACGATGCACCGCAGGATTGCCT<br>GCACTTTAGCAAGCTGATGGAAGCGGATGAGAGCGAAATGCCGGAAG<br>TGGTCATTAACAGCGATGATGTGGTGGCATTGCCGTACAGCTCTGGCA<br>CCACCGGCCTGCCGAAAGGCGTTATGCTGACCCACAAGGGTCTGGTTA<br>CGAGCGTTGCACAACAGGTGGATGGTGATAACCCGAACCTGTATATGC<br>ACTCCGAGGATGTCATGATCTGCATCCTGCCCACTGTTCCATATCTATAG<br>CCTGAACGCTGTTCTGTGTTGTGGTCTGCGTGCGGGCGTCACCATTCTG<br>ATCATGCAAAAGTTCGACATTGTGCCGTTTCTGGAGCTGATTCAGAAG<br>TATAAGGTTACGATTGGTCCGTTTGTCCCGCCGATCGTGCTGGCCATCG<br>CGAAAAGCCCGGTCGTTGACAAGTACGACTTGTCTAGCGTGCGCACCG<br>TCATGAGCGGTGCAGCGCCGCTGGGTAAAGAGTTGGAGGACGCTGTCC<br>GTGCGAAATTCCCGAACGCGAAGCTGGGTCAAGGCTATGGCATGACCG<br>AAGCCGGTCCGGTCCTGGCGATGTGTCTGGCGTTCGCCAAAGAGCCGT<br>ATGAGATTAAGTCTGGCGCATGCGGTACCGTTGTGCGTAATGCCGAGA<br>TGAAAATCGTTGACCCAGAAACGAATGCGTCTCTGCCGCGTAATCAGC<br>GTGGTGAGATTTGCATCCGTGGTGATCAGATTATGAAAGGTTACCTGA<br>ATGACCCGGAAAGCACCCGCACCACGATCGACGAAGAGGGTTGGTTG<br>CACACGGGTGACATTGGTTTCATCGACGATGACGATGAACTGTTCATT<br>GTCGATCGTTTGAAAGAAATCATTAAGTACAAAGGTTTTCAAGTTGCT<br>CCGGCGGAGTTGGAAGCACTGCTGCTGACGCACCCGACGATCAGCGAT<br>GCCGCGGTGGTTCCGATGATTGACGAGAAAGCGGGTGAAGTGCCAGTG<br>GCGTTTGTCGTGCGTACCAATGGTTTTACCACGACCGAAGAAGAAATC<br>AAACAATTTGTGAGCAAACAGGTCGTGTTCTACAAACGTATCTTCCGC<br>GTCTTCTTCGTTGACGCTATTCCGAAATCCCCGAGCGGCAAGATTTTGC<br>GTAAGGATCTGCGCGCTCGTATTGCGAGCGGCGACCTGCCGAAGTAA<br>(SEQ ID NO: 34) |
| P. crispus 4-coumarate:coA ligase (Pc4CL$^{sym}$) (Protein) | MGDCVAPKEDLIFRSKLPDIYIPKHLPLHTYCFENISKVGDKSCLINGATGE<br>TFTYSQVELLSRKVASGLNKLGIQQGDTIMLLLPNSPEYFFAFLGASYRGAI<br>STMANPFFTSAEVIKQLKASQAKLIITQACYVDKVKDYAAEKNIQIICIDDA<br>PQDCLHFSKLMEADESEMPEVVINSDDVVALPYSSGTTGLPKGVMLTHKG<br>LVTSVAQQVDGDNPNLYMHSEDVMICILPLFHIYSLNAVLCCGLRAGVTIL<br>IMQKFDIVPFLELIQKYKVTIGPFVPPIVLAIAKSPVVDKYDLSSVRTVMSG<br>AAPLGKELEDAVRAKFPNAKLGQGYGMTEAGPVLAMCLAFAKEPYEIKS<br>GACGTVVRNAEMKIVDPETNASLPRNQRGEICIRGDQIMKGYLNDPESTR<br>TTIDEEGWLHTGDIGFIDDDDELFIVDRLKEIIKYKGFQVAPAELEALLLTH<br>PTISDAAVVPMIDEKAGEVPVAFVVRTNGFTTTEEEIKQFVSKQVVFYKRI<br>FRVFFVDAIPKSPSGKILRKDLRARIASGDLPK (SEQ ID NO: 35) |

REFERENCES

1. Forkmann, G. and S. Martens, *Metabolic engineering and applications of flavonoids.* Curr Opin Biotechnol, 2001. 12(2): p. 155-60.
2. Fowler, Z. L. and M. A. Koffas, *Biosynthesis and biotechnological production of flavanones: current state and perspectives.* Appl Microbiol Biotechnol, 2009. 83(5): p. 799-808.
3. Harborne, J. B. and C. A. Williams, *Advances in flavonoid research since 1992.* Phytochemistry, 2000. 55(6): p. 481-504.
4. Knekt, P., et al., *Flavonoid intake and coronary mortality in Finland: a cohort study.* BMJ, 1996. 312(7029): p. 478-81.
5. Hollman, P. C. and M. B. Katan, *Bioavailability and health effects of dietary flavonols in man.* Arch Toxicol Suppl, 1998. 20: p. 237-48.
6. Kaneko, M., et al., *Heterologous production of flavanones in Escherichia coli: potential for combinatorial biosynthesis of flavonoids in bacteria.* J Ind Microbiol Biotechnol, 2003. 30(8): p. 456-61.
7. Leonard, E., et al., *Engineering central metabolic pathways for high-level flavonoid production in Escherichia coli.* Appl Environ Microbiol, 2007. 73(12): p. 3877-86.
8. Leonard, E., et al., *Strain improvement of recombinant Escherichia coli for efficient production of plant flavonoids.* Mol Pharm, 2008. 5(2): p. 257-65.
9. Miyahisa, I., et al., *Efficient production of (2S)-flavanones by Escherichia coli containing an artificial biosynthetic gene cluster.* Appl Microbiol Biotechnol, 2005. 68(4): p. 498-504.
10. Santos, C. N. S., W. Xiao, and G. Stephanopoulos, *Combinatorial and genomic approaches for engineering L-tyrosine production in Escherichia coli.* Manuscript in preparation, 2010.

11. Kodumal, S. J., et al., *Total synthesis of long DNA sequences: synthesis of a contiguous 32-kb polyketide synthase gene cluster.* Proc Natl Acad Sci USA, 2004. 101 (44): p. 15573-8.
12. Jayaraj, S., R. Reid, and D. V. Santi, *GeMS: an advanced software package for designing synthetic genes.* Nucleic Acids Res, 2005. 33(9): p. 3011-6.
13. Pedelacq, J. D., et al., *Engineering and characterization of a superfolder green fluorescent protein.* Nat Biotechnol, 2006. 24(1): p. 79-88.
14. Neidhardt, F. C., P. L. Bloch, and D. F. Smith, *Culture medium for enterobacteria.* J Bacteriol, 1974. 119(3): p. 736-47.
15. Schroeder, A. C., et al., *Contributions of conserved serine and tyrosine residues to catalysis, ligand binding, and cofactor processing in the active site of tyrosine ammonia lyase.* Phytochemistry, 2008. 69(7): p. 1496-506.
16. Watts, K. T., et al., *Discovery of a substrate selectivity switch in tyrosine ammonia-lyase, a member of the aromatic amino acid lyase family.* Chem Biol, 2006. 13(12): p. 1317-26.
17. Watts, K. T., P. C. Lee, and C. Schmidt-Dannert, *Exploring recombinant flavonoid biosynthesis in metabolically engineered Escherichia coli.* Chembiochem, 2004. 5(4): p. 500-7.
18. Fowler, Z. L., W. W. Gikandi, and M. A. Koffas, *Increased malonyl coenzyme A biosynthesis by tuning the Escherichia coli metabolic network and its application to flavanone production.* Appl Environ Microbiol, 2009. 75(18): p. 5831-9.
19. Kane, J. F., *Effects of rare codon clusters on high-level expression of heterologous proteins in Escherichia coli.* Curr Opin Biotechnol, 1995. 6(5): p. 494-500.
20. Vannelli, T., et al., *Production of p-hydroxycinnamic acid from glucose in Saccharomyces cerevisiae and Escherichia coli by expression of heterologous genes from plants and fungi.* Metab Eng, 2007. 9(2): p. 142-51.
21. Xue, Z., et al., *Identification, characterization and functional expression of a tyrosine ammonia-lyase and its mutants from the photosynthetic bacterium Rhodobacter sphaeroides.* J Ind Microbiol Biotechnol, 2007. 34(9): p. 599-604.
22. Xue, Z., et al., *Improved production of p-hydroxycinnamic acid from tyrosine using a novel thermostable phenylalanine/tyrosine ammonia lyase enzyme.* Enzyme and Microbial Technology, 2007. 42(1): p. 58-64.
23. Sariaslani, F. S., *Development of a combined biological and chemical process for production of industrial aromatics from renewable resources.* Annu Rev Microbiol, 2007. 61: p. 51-69.
24. Takamura, Y. and G. Nomura, *Changes in the intracellular concentration of acetyl-CoA and malonyl-CoA in relation to the carbon and energy metabolism of Escherichia coli K12.* J Gen Microbiol, 1988. 134(8): p. 2249-53.
25. Ajikumar, P. K., et al., *Isoprenoid pathway optimization by a multivariate-modular approach for Taxol precursor overproduction in Escherichia coli.* Manuscript submitted.
26. Alper, H., et al., *Tuning genetic control through promoter engineering.* Proc Natl Acad Sci USA, 2005. 102(36): p. 12678-83.
27. Pfleger, B. F., et al., *Combinatorial engineering of intergenic regions in operons tunes expression of multiple genes.* Nat Biotechnol, 2006. 24(8): p. 1027-32.

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety for the purposes cited herein.

We claim:

1. An isolated cell that recombinantly expresses genes encoding tyrosine ammonia lyase (TAL), 4-coumarate:CoA ligase (4CL), chalcone synthase (CHS), and chalcone isomerase (CHI), and wherein the cell produces one or more flavonoids or naringenin from glucose without additional precursor supplementation, and wherein the expression of the genes encoding TAL, 4CL, CHS and CHI is balanced in the cell by constitutive expression of CHS and CHI.

2. The isolated cell of claim 1, wherein the gene encoding TAL is a yeast gene or a bacterial gene.

3. The isolated cell of claim 1, wherein the gene encoding 4CL is a plant gene or a bacterial gene.

4. The isolated cell of claim 1, wherein the at least one of the gene encoding CHS and the gene encoding CHI is a plant gene.

5. The isolated cell of claim 1, wherein the genes encoding at least one of TAL, 4CL, CHS, and CHI are expressed from a single polycistronic operon, or wherein each of the genes is expressed from a separate promoter.

6. The isolated cell of claim 1, wherein the cell is a prokaryotic cell.

7. The isolated cell of claim 6, wherein the endogenous L-tyrosine production is at least 250 milligrams/liter.

8. The isolated cell of claim 6, wherein the cell is a bacterial cell.

9. The isolated cell of claim 1, wherein at least one of the genes encoding TAL, 4CL, CHS, and CHI is a synthetic gene that is codon optimized for expression in bacteria.

10. The isolated cell of claim 1, wherein the cell is a eukaryotic cell.

11. The isolated cell of claim 1, wherein at least one of the genes encoding TAL, 4CL, CHS, and CHI are expressed on plasmids, or wherein at least one of the genes encoding TAL, 4CL, CHS, and CHI are integrated into the genome of the cell.

12. The isolated cell of claim 1, wherein the production of naringenin is increased by protein engineering of at least one of the TAL, 4CL, CHS, and CHI in the cell.

13. The isolated cell of claim 1, wherein the cell further comprises a recombinantly-expressed malonate assimilation pathway.

14. The isolated cell of claim 1, wherein the cell further comprises simultaneous deletions of genes encoding succinate dehydrogenase, alcohol/acetaldehyde dehydrogenase, branched chain amino acid transporter, and citrate lyase and overexpresses the enzymes acetyl-CoA synthase, acetyl-CoA carboxylase, biotin ligase, and pantothenate kinase.

15. The isolated cell of claim 1, wherein upon culturing the cell produces at least 500 micrograms/liter naringenin in the culture medium.

16. A method for producing one or more flavonoids or naringenin comprising
    culturing the cell of claim 1 to produce the one or more flavonoids or the naringenin.

17. The method of claim 16, wherein the culture medium is not supplemented with a precursor of naringenin synthesis.

18. The method of claim 16, wherein the cells are cultured in the presence of the fatty acid pathway inhibitor cerulenin or wherein the cell culture is supplemented with malonate.

19. The method of claim 16, wherein the cells produce at least 500 micrograms/liter naringenin in the culture medium.

* * * * *